United States Patent
Anderskewitz et al.

(10) Patent No.: US 9,073,869 B2
(45) Date of Patent: Jul. 7, 2015

(54) METHOD OF USING SUBSTITUTED 2-AZA-BICYCLO[2.2.2]OCTANE-3-CARBOXYLIC ACID (BENZYL-CYANO-METHYL)-AMIDES INHIBITORS OF CATHEPSIN C

(71) Applicants: Ralf Anderskewitz, Laupheim (DE); Matthias Grauert, Biberach an der Riss (DE); Marc Grundl, Biberach an der Riss (DE); Thorsten Oost, Biberach an der Riss (DE); Alexander Pautsch, Biberach an der Riss (DE); Stefan Peters, Biberach an der Riss (DE)

(72) Inventors: Ralf Anderskewitz, Laupheim (DE); Matthias Grauert, Biberach an der Riss (DE); Marc Grundl, Biberach an der Riss (DE); Thorsten Oost, Biberach an der Riss (DE); Alexander Pautsch, Biberach an der Riss (DE); Stefan Peters, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/483,217

(22) Filed: Sep. 11, 2014

(65) Prior Publication Data

US 2014/0378504 A1 Dec. 25, 2014

Related U.S. Application Data

(62) Division of application No. 14/205,867, filed on Mar. 12, 2014, now Pat. No. 8,877,775.

(30) Foreign Application Priority Data

Mar. 14, 2013 (EP) .................... 13159242
May 31, 2013 (EP) .................... 13170006

(51) Int. Cl.
| | | |
|---|---|---|
| A61K 31/439 | (2006.01) |
| A61K 31/4725 | (2006.01) |
| A61K 45/06 | (2006.01) |
| C07D 221/22 | (2006.01) |
| C07D 401/12 | (2006.01) |
| C07D 417/12 | (2006.01) |
| C07D 453/06 | (2006.01) |

(52) U.S. Cl.
CPC ............ *C07D 221/22* (2013.01); *A61K 31/439* (2013.01); *A61K 31/4725* (2013.01); *A61K 45/06* (2013.01); *C07D 401/12* (2013.01); *C07D 417/12* (2013.01); *C07D 453/06* (2013.01)

(58) Field of Classification Search
CPC .. A61K 31/439; A61K 31/4725; A61K 45/06
USPC .......................................... 546/152; 514/311
See application file for complete search history.

(56) References Cited

U.S. PATENT DOCUMENTS

| 4,125,727 A | 11/1978 | Los |
| 7,012,075 B2 | 3/2006 | Prasit et al. |
| 7,902,181 B2 | 3/2011 | Furber et al. |
| 2006/0223846 A1 | 10/2006 | Dyatkin et al. |
| 2013/0172327 A1 | 7/2013 | Grundl et al. |

FOREIGN PATENT DOCUMENTS

| WO | 0202556 A2 | 1/2002 |
| WO | 2004110988 A1 | 12/2004 |
| WO | 2005042533 A2 | 5/2005 |
| WO | 2009047829 A1 | 4/2009 |
| WO | 2009074829 A1 | 6/2009 |
| WO | 2010128324 A1 | 11/2010 |
| WO | 2010142985 A1 | 12/2010 |
| WO | 2012119941 A1 | 9/2012 |
| WO | 2013041497 A1 | 3/2013 |

OTHER PUBLICATIONS

Abstract in English for WO 2009/047829, publication date Apr. 16, 2009.
Adkison, A.M. et al., "Dipeptidyl peptidase I activates neutrophil-derived serine proteases and regulates the development of acute experimental arthritis." The Journal of Clinical Investigation, 2002, vol. 109, No. 3, pp. 363-371.
Akk, A.M. et al., "Dipeptidyl Peptidase I-Dependent Neutrophil Recruitment Modulates the Inflammatory Response to Sendai Virus Infection." The Journal of Immunology, 2008, vol. 180, pp. 3535-3542.

(Continued)

*Primary Examiner* — Niloofar Rahmani
(74) *Attorney, Agent, or Firm* — Michael P. Morris; Atabak R. Royaee

(57) ABSTRACT

This invention relates to 2-Aza-bicyclo[2.2.2]octane-3-carboxylic acid (benzyl-cyano-methyl)-amides of formula 1

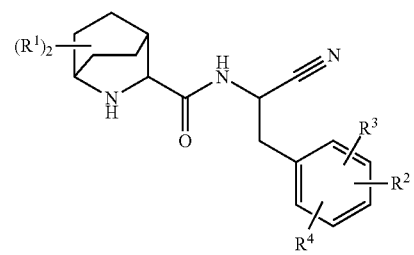

and their use as inhibitors of Cathepsin C, pharmaceutical compositions containing the same, and methods of using the same as agents for treatment and/or prevention of diseases connected with dipeptidyl peptidase I activity, e.g. respiratory diseases.

13 Claims, No Drawings

(56) References Cited

OTHER PUBLICATIONS

Bondebjerg, J. et al., "Dipeptidyl nitriles as human dipeptidyl peptidase I inhibitors." Bioorganic & Medicinal Chemistry Letters, 2006, vol. 16, No. 13, pp. 3614-3617.
Farberman, M.M. et al., "Airway proteins involved in bacterial clearance susceptible to cathepsin G proteolysis." European Respiratory Journal, 2010, vol. 35, No. 2, pp. 410-417.
Guay, D. et al., "Design and synthesis of dipeptidyl nitriles as potent, selective, and reversible inhibitors of cathespin C." Bioorganic & Medicinal Chemistry Letters, 2009, vol. 19, No. 18, pp. 5392-5396.
Guyot, N. et al., "Deficiency in All Three Neutrophil Serine Proteases Protects Mice Against Cigarette Smoke-Induced Emphysema." American Journal of Respiratory and Critical Care Medicine, 2010, vol. 181, p. A5128.
Henriksen, P.A. et al., "Human neutrophil elastase: Mediator and therapeutic target in atherosclerosis." The International Journal of Biochemistry & Cell Biology, 2008, vol. 40, pp. 1095-1100.
Herias, M. et al., "Abstract 5871: Leukocyte Cathepsin C Deficiency Attenuates Atherosclerosis in LDL Receptor Deficient Mice." Circulation, 2009, vol. 120, p. 1166.
Hu, Y. et al., "Dipeptidyl Peptidase I Regulates the Development of Collagen-Induced Arthritis." Arthritis & Rheumatism, 2005, vol. 52, No. 8, pp. 2553-2558.
International Search Report for PCT/EP2014/054794 mailing date Apr. 2, 2014.
International Search Report for PCT/EP2014/054798 mailing date Apr. 4, 2014.
International Search Report for PCT/EP2014/054802 mailing date Apr. 10, 2014.
International Search Report for PCT/EP2014/054827 mailing date Apr. 28, 2014.
Joosten, L.A. et al., "Inflammatory Arthritis in Caspase 1 Gene-Deficient Mice." Arthritis & Rheumatism, 2009, vol. 60, No. 12, pp. 3651-3662.
Koga, H. et al., "Inhibition of neutrophil elastase attenuates airway hyperresponsiveness and inflammation in a mouse model of secondary allergen challenge: neutrophil elastase inhibition attenuates allergic airway responses." Respiratory Research, 2013, vol. 14, No. 8, pp. 1-13.
Kotlowski, R. et al., "Population-Based Case-Control Study of Alpha 1-Antitrypsin and SLC11A1 in Crohn's Disease and Ulcerative Colitis." Inflammatory Bowel Disease, 2008, vol. 14, No. 8, pp. 1112-1117.
Laprise, C. et al., "Functional classes of bronchial mucosa genes that are differentially expressed in asthma." BMC Genomics, 2004, vol. 5, No. 21, pp. 1-10.
Liu, H. et al., "Neutrophil elastase and elastase-rich cystic fibrosis sputum degranulate human eosinophils in vitro." American Physiological Scoiety, 1999, vol. 276, pp. L28-L34.
Milner, J.M. et al., "Emerging Roles of Serine Proteinases in Tissue Turnover in Arthritis." Arthritis & Rheumatism, 2008, vol. 58, No. 12, pp. 3644-3656.
Morohoshi, Y. et al., "Inhibition of neutrophil elastase prevents the development of murine dextran sulfate sodium-induced colitis." Journal of Gastroenterology, 2006, vol. 41, pp. 318-324.
Motta, Jean-Paul et al., "Modifying the Protease, Antiprotease Pattern by Elafin Overexpression Protects Mice From Colitis." Gastroenterology, 2011, vol. 140, pp. 1272-1282.
Schmid, M. et al., "Attenuated induction of epithelial and leukocyte serine antiproteases elafin and secretory leukocyte protease inhibitor in Crohn's disease." Journal of Leukocyte Biology, 2007, vol. 81, pp. 907-915.
Sedor, J. et al., "Cathepsin-G Interferes with Clearance of *Pseudomonas aeruginosa* from Mouse Lungs." Pediatric Research, 2007, vol. 61, No. 1, pp. 26-31.
Shapiro, S.D. et al., "Neutrophil Elastase Contributes to Cigarette Smoke-Induced Emphysema in Mice." American Journal of Pathology, 2003, vol. 163, No. 6, pp. 2329-2335.
Wright, J.L. et al., "Synthetic Serine Elastase Inhibitor Reduces Cigarette Smoke-Induced Emphysema in Guinea Pigs." Ameican Journal of Respiratory and Critical Care Medicine, 2002, vol. 166, pp. 954-960.
Yuyama, N. et al., "Analysis of Novel Disease-Related Genes in Bronchial Asthma." Cytokine, 2002, vol. 19, No. 6, pp. 287-296.

METHOD OF USING SUBSTITUTED 2-AZA-BICYCLO[2.2.2]OCTANE-3-CARBOXYLIC ACID (BENZYL-CYANO-METHYL)-AMIDES INHIBITORS OF CATHEPSIN C

FIELD OF INVENTION

This invention relates to 2-Aza-bicyclo[2.2.2]octane-3-carboxylic acid (benzyl-cyano-methyl)-amides of formula 1

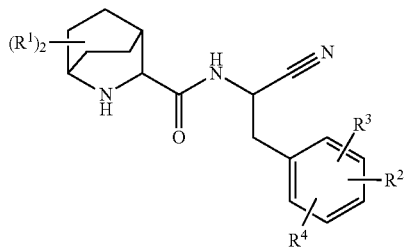

1 and their use as inhibitors of Cathepsin C, pharmaceutical compositions containing the same, and methods of using the same as agents for treatment and/or prevention of diseases connected with dipeptidyl peptidase I activity, e.g. respiratory diseases.

BACKGROUND INFORMATION

WO2004110988 discloses peptidyl nitrile inhibitors as dipeptidyl-peptidase I (DPPI) inhibitors for the treatment of a series of diseases.

WO2009074829 and WO2010142985 also disclose peptidyl nitrile inhibitors as dipeptidyl-peptidase I (DPPI) inhibitors for the treatment asthma, COPD or allergic rhinitis.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains. DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci 96: 8627-8632, 1999), mast cells (chymase and tryptase; Wolter et al.; J Biol. Chem. 276: 18551-18556, 2001), and neutrophils (Cathepsin G, elastase and proteinase 3; Adkison et al.; J Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J Clin. Invest. 109: 363.371, 2002).

In light of the role DPPI plays in activating certain pro-inflammatory serine proteases, it seems desirable to prepare compounds that inhibit its activity, which thereby inhibit downstream serine protease activity. It has been surprisingly found that the bicyclic compounds of the present invention possess potent Cathepsin C activity, high selectivity against other Cathepsins, e.g. Cathepsin K, and in general desirable pharmacokinetic properties.

DETAILED DESCRIPTION OF THE INVENTION

A compound of formula 1

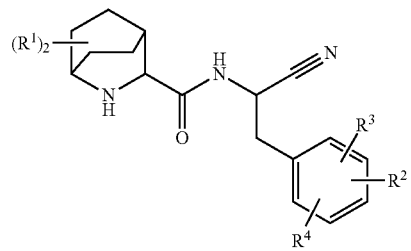

1 wherein
$R^1$ is independently selected from among H, $C_{1-6}$-alkyl-, halogen, HO—, $C_{1-6}$-alkyl-O—, $H_2N$—, $C_{1-6}$-alkyl-HN—, $(C_{1-6}$-alkyl$)_2N$— and $C_{1-6}$-alkyl-C(O)HN—;
or two $R^1$ are together $C_{1-4}$-alkylene;
$R^2$ is selected from among
  $R^{2.1}$;
  aryl-; optionally substituted with one, two or three residues independently selected from $R^{2.1}$; optionally substituted with one $R^{2.3}$;
  $C_{5-10}$-heteroaryl-; containing one, two, three or four heteroatoms independently selected from among S, S(O), $S(O)_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$; and $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$ or $R^2$ and $R^4$ are together with two adjacent carbon atoms of the phenyl ring a 5- or 6-membered aryl or heteroaryl, containing one, two or three heteroatoms independently selected from among S, S(O), S(O)$_2$, O and N, wherein carbon atoms of the ring are optionally and independently from each other substituted with one, two or three $R^{2.1}$;

wherein nitrogen atoms of the ring are optionally and independently from each other substituted with one, two or three $R^{2.2}$;

$R^{2.1}$ is independently selected from among H, halogen, NC—, O=, HO—, H-A-, H-A-$C_{1-6}$-alkylene-, $R^{2.1.1}$-A-, $C_{1-6}$-alkyl-A-, $C_{3-8}$-cycloalkyl-A-, $C_{1-6}$-haloalkyl-A-, $R^{2.1.1}$—$C_{1-6}$-alkylene-A-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$—$C_{1-6}$-alkylene-A-$C_{1-6}$-alkylene-, $R^{2.1.1}$-A-$C_{1-6}$-alkylene-, HO—$C_{1-6}$-alkylene-A-, HO—$C_{1-6}$-alkylene-A-$C_{1-6}$-alkylene-, $C_{1-6}$-alkyl-O—$C_{1-6}$-alkylene-A- and $C_{1-6}$-alkyl-O—$C_{1-6}$-alkylene-A-$C_{1-6}$-alkylene- $R^{2.1.1}$ is independently selected from among aryl-; optionally substituted independently from each other with one, two or three $R^{2.1.1.1}$;

$C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1.1.1}$; wherein nitrogen atoms of the ring are optionally and independently from each other substituted with one, two or three $R^{2.1.1.2}$;

$R^{2.1.1.1}$ is independently selected from among halogen, HO—, O=, $C_{1-6}$-alkyl-, $C_{1-6}$-alkyl-O—, $C_{1-6}$-haloalkyl-, $C_{1-6}$-haloalkyl-O— and $C_{3-8}$-cycloalkyl-;

$R^{2.1.1.2}$ is independently selected from among O=, $C_{1-6}$-alkyl-, $C_{1-6}$-haloalkyl-; $C_{3-8}$-cycloalkyl-, $C_{1-6}$-alkyl-O—$C_{1-6}$-alkyl-, H(O)C—, $C_{1-6}$-alkyl-(O)C—, tetrahydrofuranylmethyl- and tetrahydropyranylmethyl-;

$R^{2.2}$ is independently selected from among H-A-$C_{1-6}$-alkylene-, $C_{3-8}$-cycloalkyl-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $C_{1-6}$-alkyl-S(O)$_2$—, $C_{1-6}$-alkyl-C(O)— and $R^{2.1.1}$-A-;

$R^{2.3}$ and $R^4$ are together selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, $R^{2.3}$, $R^{2.3}$, —C($R^{2.3.2}$)=C($R^{2.3}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-;

$R^{2.3.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4}$ and $R^4$ are together selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, —N($R^{2.4.1}$)C($R^{2.4.2}$)$_2$— and —$C_{1-4}$-alkylene-; and $R^{2.4.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.5}$ and $R^4$ are together selected from among —C($R^{2.5.1}$)=, =C($R^{2.5.1}$)— and —N=; and $R^{2.5.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^3$ is H or F;

$R^4$ is independently selected from among H, F, Cl, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene-, ($C_{1-6}$-alkyl)$_2$-HN—$C_{1-4}$-alkylene-; preferably F, Cl, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=)S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, —S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from among H, $C_{1-6}$-alkyl- and NC—;

or a salt thereof.

Preferred Embodiments

Preferred are the above compounds of formula 1, wherein $R^1$ is $R^{1.a}$ and $R^{1.a}$ is independently selected from among H, $C_{1-4}$-alkyl-, F— and HO—.

Preferred are the above compounds of formula 1, wherein $R^1$ is $R^{1.b}$ and $R^{1.b}$ is H.

Preferred are the above compounds of formula 1, wherein $R^1$ is $R^{1.c}$ and two $R^{1.c}$ are together —CH$_2$—.

Preferred are the above compounds of formula 1, wherein $R^2$ is $R^{2.a}$ and $R^{2.a}$ is $R^{2.1}$.

Preferred are the above compounds of formula 1, wherein $R^2$ is $R^{2.b}$ and $R^{2.b}$ is $R^{2.1.a}$.

Preferred are the above compounds of formula 1, wherein $R^2$ is $R^{2.c}$ and $R^{2.c}$ is aryl-; optionally substituted with one, two or three residues independently selected from $R^{2.1}$; optionally substituted with one $R^{2.3}$.

Preferred are the above compounds of formula 1, wherein $R^2$ is $R^{2.d}$ and $R^{2.d}$ is phenyl; optionally substituted with one, two or three residues independently selected from $R^{2.1}$; optionally substituted with one $R^{2.3}$.

Preferred are the above compounds of formula 1, wherein $R^2$ is $R^{2.e}$ and $R^{2.e}$ is $C_{5\ or\ 6}$-heteroaryl-, containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.f}$ and $R^{2.f}$ is bicyclic $C_{7-10}$-heteroaryl-, each containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.g}$ and $R^{2.g}$ is selected from among

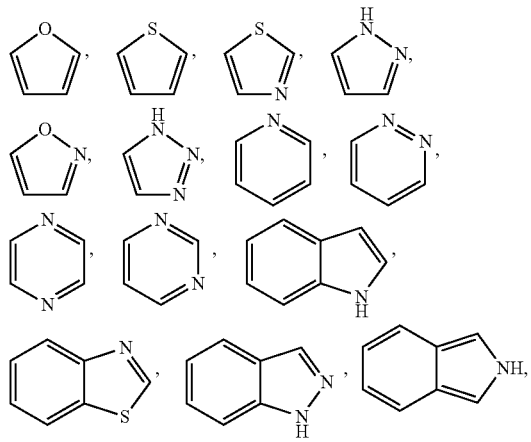

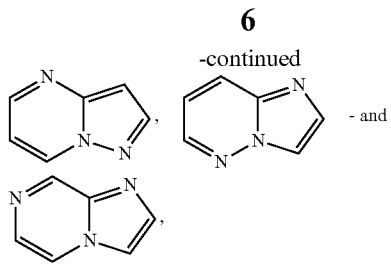

wherein carbon atoms of the ring are optionally and independently from each other substituted with one, two or three $R^{2.1}$, wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.g}$ and $R^{2.g}$ is selected from among

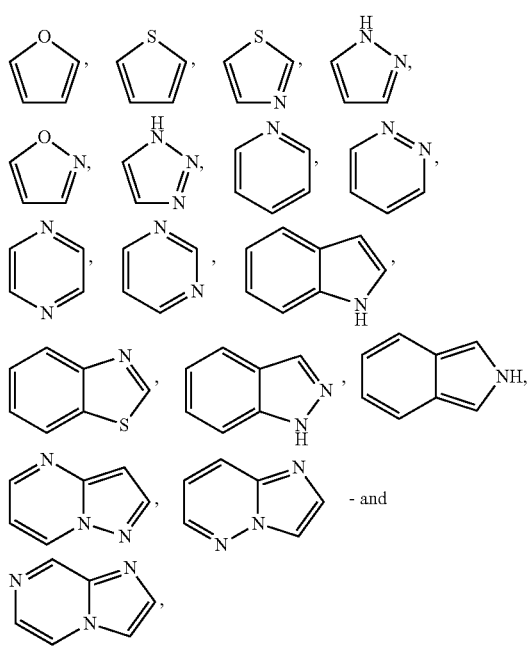

wherein carbon atoms of the ring are optionally and independently from each other substituted with one, two or three $R^{2.1}$; wherein possibly available nitrogen atoms of the ring are optionally and independently from each other substituted with $R^{2.2}$; and $R^{2.1}$ is $R^{2.1.a}$ and $R^{2.1.a}$ is selected from among H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
   aryl-, optionally substituted independently from each other with one, two or three residues independently selected from $R^{2.1.1.1}$;
   $C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), $S(O)_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl- and $C_{1-4}$-haloalkyl-O—, $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

Preferred are the above compounds of formula 1, wherein $R^2$ is $R^{2.h}$ and $R^{2.h}$ is selected from among pyrazole, thiophene- and furane, wherein carbon atoms of the ring are optionally and independently from each other substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.i}$ and $R^{2.i}$ is selected from among $C_6$-heterocyclyl- and $C_{7-10}$-heterocyclyl-, each containing one, two, three or four heteroatoms independently selected from among S, O and N and the ring is fully or partially saturated, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.j}$ and $R^{2.j}$ is selected from among

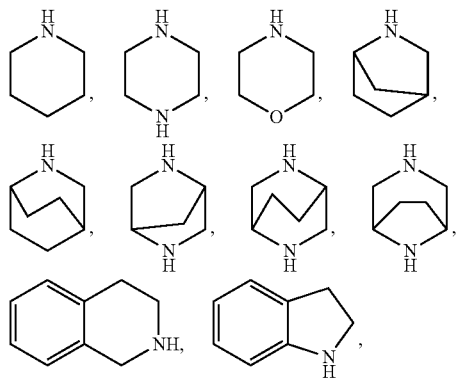

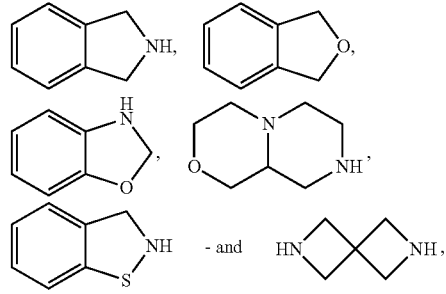

-continued

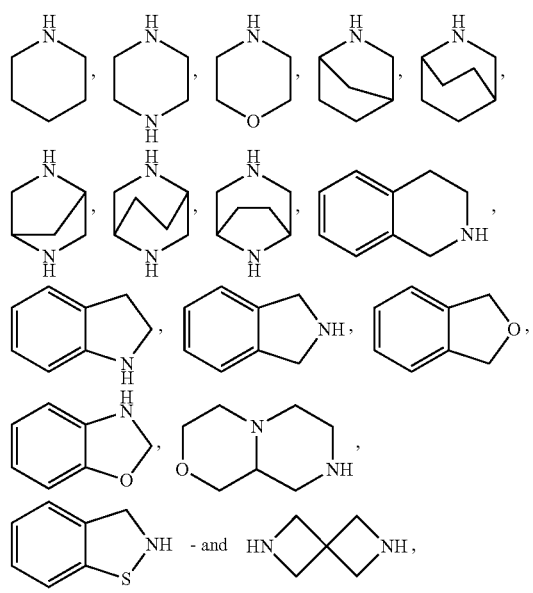

wherein carbon atoms of the ring are optionally and independently from each other substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.j}$ and $R^{2.j}$ is selected from among wherein carbon atoms of the ring are optionally and independently from each other substituted with one, two or three $R^{2.1}$; possibly available nitrogen atoms of the ring are optionally and independently from each other substituted with $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; — and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

Preferred are the above compounds of formula 1, wherein $R^2$ is $R^{2.k}$ and $R^{2.k}$ is selected from among

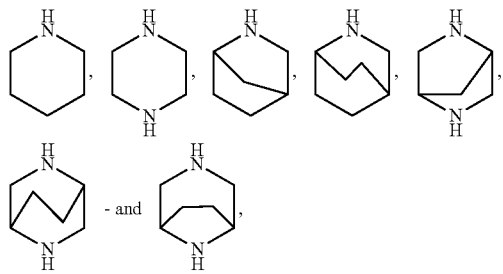

wherein carbon atoms of the ring are optionally and independently from each other substituted with one, two or three $R^{2.1}$; possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.1}$ and $R^{2.1}$ is selected from among

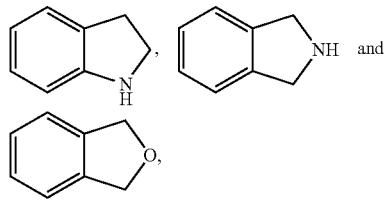

wherein carbon atoms of the ring are optionally and independently from each other substituted with one, two, three or four $R^{2.1}$; possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from among S, S(O), S(O)$_2$, O and N, preferably pyrazole- and naphtene, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$.

Preferred are the above compounds of formula 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from among S, S(O), S(O)$_2$, O and N, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; — and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

Preferred are the above compounds of formula 1, wherein $R^2$ is $R^{2.n}$ and $R^{2.n}$ is selected from among aryl-, pyrazole, thiophene- and furane; wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from among

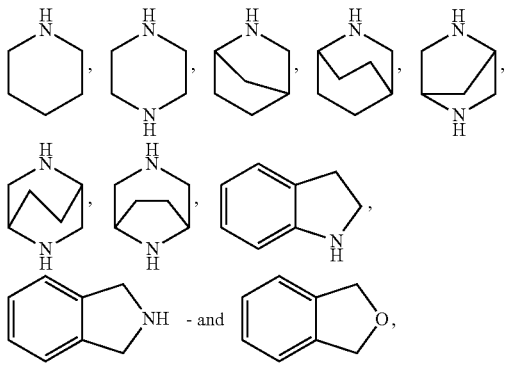

wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.n}$ and $R^{2.n}$ is selected from among aryl-, pyrazole, thiophene- and furane; wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from among

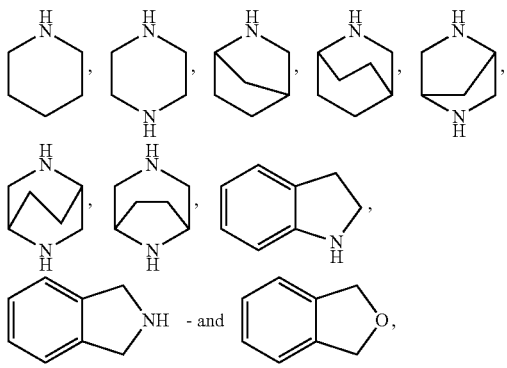

wherein carbon atoms of the ring are optionally and independently from each other substituted with one, two, three or four $R^{2.1}$, wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
aryl-, optionally substituted independently from each other with one, two or three residues independently selected from $R^{2.1.1.1}$;
$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O—, $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$— and $C_{1-4}$-alkyl-C(O)—, $R^{2.1.1}$-A-; and $R^{2.3}$ is together with $R^4$ a group $R^{2.3.a}$ and $R^{2.3.a}$ is selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-; and $R^{2.4}$ is together with $R^4$ a group $R^{2.4.a}$ and $R^{2.4.a}$ is selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C(R$^{2.4.2}$)=C(R$^{2.4.2}$)—, —C=N—, —N=C—, —C(R$^{2.4.2}$)$_2$N(R$^{2.4.1}$)—, —N(R$^{2.4.1}$)C(R$^{2.4.2}$)$_2$— and —C$_{1-4}$-alkylene-; and R$^{2.4.1}$ is independently selected from among H, C$_{1-4}$-alkyl-, C$_{1-4}$-haloalkyl-, C$_{3-6}$-cycloalkyl-, HO—C$_{1-4}$-alkylene- and (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene-, (C$_{1-4}$-alkyl)$_2$N—C$_{1-4}$-alkylene-; R$^{2.4.2}$ is independently selected from among H, C$_{1-4}$-alkyl-, C$_{1-4}$-haloalkyl-, C$_{3-6}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-; and R$^{2.5}$ is together with R$^4$ a group R$^{2.5.a}$ and R$^{2.5.a}$ is selected from among —C(R$^{2.5.1}$)=, =C(R$^{2.5.1}$)— and —N=; and R$^{2.5.1}$ is independently selected from among H, C$_{1-4}$-alkyl-, C$_{1-4}$-haloalkyl-, C$_{3-6}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-.

Preferred are the above compounds of formula 1, wherein R$^2$ is R$^{2.o}$ and R$^{2.o}$ is selected from among aryl-, pyrazole, thiophene- and furane; wherein carbon atoms of the ring are optionally and independently from each other substituted with one, two, three or four R$^{2.1}$; wherein possibly available nitrogen atoms of the ring are optionally and independently from each other substituted with R$^{2.2}$; wherein a carbon atom of the ring is optionally substituted with one R$^{2.3}$; a nitrogen atom of the ring is optionally substituted with one R$^{2.4}$.

Preferred are the above compounds of formula 1, wherein R$^2$ is R$^{2.p}$ and R$^{2.p}$ is selected from among

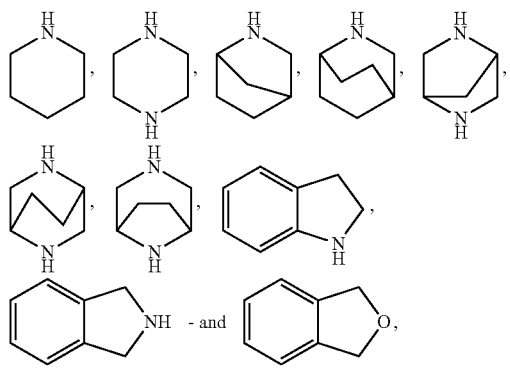

wherein carbon atoms of the ring are optionally and independently from each other substituted with one, two, three or four R$^{2.1}$; wherein possibly available nitrogen atoms of the ring are optionally and independently from each other substituted with R$^{2.2}$; wherein a carbon atom of the ring is optionally substituted with one R$^{2.3}$ or one R$^{2.5}$; a nitrogen atom of the ring is optionally substituted with one R$^{2.4}$.

Preferred are the above compounds of formula 1, wherein R$^{2.1}$ is R$^{2.1.a}$ and R$^{2.1.a}$ is selected from among H, halogen, NC—, O=, HO—, H-A-, H-A-C$_{1-4}$-alkylene-, R$^{2.1.1}$-A-, C$_{1-4}$-alkyl-A-, C$_{3-6}$-cycloalkyl-A-, C$_{1-4}$-haloalkyl-A-, R$^{2.1.1}$—C$_{1-4}$-alkylene-A-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, R$^{2.1.1}$—C$_{1-4}$-alkylene-A-C$_{1-4}$-alkylene-, R$^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-.

Preferred are the above compounds of formula 1, wherein R$^{2.1.1}$ is R$^{2.1.1.a}$ and R$^{2.1.1.a}$ is selected from among aryl-, optionally substituted independently from each other with one, two or three residues independently selected from R$^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; and C$_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; and R$^{2.1.1.1}$ is independently selected from among halogen, HO—, O=, C$_{1-4}$-alkyl-, C$_{1-4}$-alkyl-O—, C$_{1-4}$-haloalkyl- and C$_{1-4}$-haloalkyl-O—, C$_{3-6}$-cycloalkyl-; and R$^{2.1.1.2}$ is independently selected from among O=, C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl.

Preferred are the above compounds of formula 1, wherein R$^{2.1.1}$ is R$^{2.1.1.b}$ and R$^{2.1.1.b}$ is phenyl or selected from among

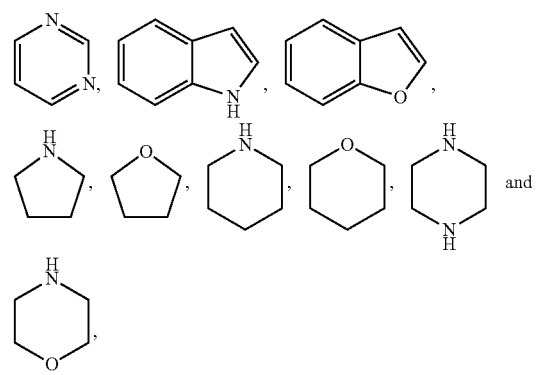

wherein carbon atoms of the ring are optionally and independently from each other substituted with one, two or three R$^{2.1.1.1}$, wherein possibly available nitrogen atoms of the ring are optionally and independently from each other substituted with R$^{2.1.1.2}$; and R$^{2.1.1.1}$ is independently selected from among halogen, HO—, O=, C$_{1-4}$-alkyl-, C$_{1-4}$-alkyl-O—, C$_{1-4}$-haloalkyl- and C$_{1-4}$-haloalkyl-O—, C$_{3-6}$-cycloalkyl-; and R$^{2.1.1.2}$ is independently selected from among O=, C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl.

Preferred are the above compounds of formula 1, wherein R$^{2.1.1}$ is R$^{2.1.1.c}$ and R$^{2.1.1.c}$ is phenyl or selected from among

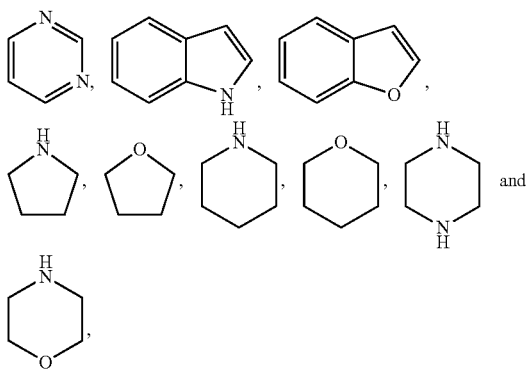

wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and $R^{2.1.1.1}$ is independently selected from among F, Cl, Me, MeO— and cyclopropyl-; and $R^{2.1.1.2}$ is independently selected from among Me, tetrahydrofuranylmethyl- and tetrahydropyranylmethyl.

Preferred are the above compounds of formula 1, wherein $R^{2.1.2}$ is $R^{2.1.2.a}$ and $R^{2.1.2.a}$ is selected from among H, NC—, $C_{1-4}$-alkyl-, $C_{1-4}$-haloalkyl-, $C_{3-6}$-cycloalkyl-, HO—$C_{1-4}$-alkylene- and ($C_{1-4}$-alkyl)-O—$C_{1-4}$-alkylene-.

Preferred are the above compounds of formula 1, wherein $R^{2.1.2}$ is $R^{2.1.2.b}$ and $R^{2.1.2.b}$ is selected from among H, $C_{1-4}$-alkyl- and $C_{3-6}$-cycloalkyl-;

Preferred are the above compounds of formula 1, wherein $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-;

Preferred are the above compounds of formula 1, wherein $R^{2.2}$ is $R^{2.2.b}$ and $R^{2.2.b}$ is together with $R^4$ selected from among —C(O)—, —S(O)—, —S(O)$_2$—, —C($R^{2.1.2}$)=C($R^{2.1.2}$)— and —$C_{1-4}$-alkylene-;

Preferred are the above compounds of formula 1, wherein $R^{2.3}$ is together with $R^4$ a group $R^{2.3.a}$ and $R^{2.3.a}$ is selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^{2.4}$ is together with $R^4$ a group $R^{2.4.a}$ and $R^{2.4.a}$ is selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, —N($R^{2.4.1}$)C($R^{2.4.2}$)$_2$— and —$C_{1-4}$-alkylene-; and $R^{2.4.1}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^{2.5}$ is together with $R^4$ a group $R^{2.5.a}$ and $R^{2.5.a}$ is selected from among —C($R^{2.5.1}$)=, =C($R^{2.5.1}$)— and —N=; and $R^{2.5.1}$ is independently selected from among H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^2$ is selected from the Table 1 $R^2$—Embodiments of the invention for $R^2$, $R^{2.1}$, $R^{2.1.1}$, $R^{2.2}$, $R^{2.3}$, $R^{2.4}$ and $R^{2.5}$ (if present):

TABLE 1

| E# | $R^2$ | $R^{2.1}$ | $R^{2.1.1}$ | $R^{2.2}$ | $R^{2.3-5}$ |
|----|-------|-----------|-------------|-----------|-------------|
| 1  | $R^{2.a}$ | $R^{2.1}$ | $R^{2.1.1.a}$ | — | — |
| 2  | $R^{2.a}$ | $R^{2.1}$ | $R^{2.1.1.b}$ | — | — |
| 3  | $R^{2.a}$ | $R^{2.1}$ | $R^{2.1.1.c}$ | — | — |
| 4  | $R^{2.b}$ | $R^{2.1.a}$ | $R^{2.1.1.a}$ | — | — |
| 5  | $R^{2.b}$ | $R^{2.1.a}$ | $R^{2.1.1.b}$ | — | — |
| 6  | $R^{2.b}$ | $R^{2.1.a}$ | $R^{2.1.1.c}$ | — | — |
| 7  | $R^{2.c}$ | $R^{2.1.a}$ | $R^{2.1.1.a}$ | — | — |
| 8  | $R^{2.c}$ | $R^{2.1.a}$ | $R^{2.1.1.b}$ | — | — |
| 9  | $R^{2.c}$ | $R^{2.1.a}$ | $R^{2.1.1.c}$ | — | — |
| 10 | $R^{2.c}$ | $R^{2.1.a}$ | $R^{2.1.1.c}$ | — | $R^{2.3.a}$ |
| 11 | $R^{2.c}$ | $R^{2.1.a}$ | $R^{2.1.1.c}$ | — | $R^{2.4.a}$ |
| 12 | $R^{2.c}$ | $R^{2.1.a}$ | $R^{2.1.1.c}$ | — | $R^{2.5.a}$ |
| 13 | $R^{2.d}$ | $R^{2.1.a}$ | $R^{2.1.1.a}$ | — | — |
| 14 | $R^{2.d}$ | $R^{2.1.a}$ | $R^{2.1.1.b}$ | — | — |
| 15 | $R^{2.d}$ | $R^{2.1.a}$ | $R^{2.1.1.c}$ | — | — |
| 16 | $R^{2.d}$ | $R^{2.1.a}$ | $R^{2.1.1.c}$ | — | $R^{2.3.a}$ |
| 17 | $R^{2.d}$ | $R^{2.1.a}$ | $R^{2.1.1.c}$ | — | $R^{2.4.a}$ |
| 18 | $R^{2.d}$ | $R^{2.1.a}$ | $R^{2.1.1.c}$ | — | $R^{2.5.a}$ |
| 19 | $R^{2.e}$ | $R^{2.1.a}$ | $R^{2.1.1.a}$ | $R^{2.2.a}$ | — |
| 20 | $R^{2.e}$ | $R^{2.1.a}$ | $R^{2.1.1.b}$ | $R^{2.2.a}$ | — |
| 21 | $R^{2.e}$ | $R^{2.1.a}$ | $R^{2.1.1.c}$ | $R^{2.2.a}$ | — |
| 22 | $R^{2.f}$ | $R^{2.1.a}$ | $R^{2.1.1.a}$ | $R^{2.2.a}$ | — |
| 23 | $R^{2.f}$ | $R^{2.1.a}$ | $R^{2.1.1.b}$ | $R^{2.2.a}$ | — |
| 24 | $R^{2.f}$ | $R^{2.1.a}$ | $R^{2.1.1.c}$ | $R^{2.2.a}$ | — |
| 25 | $R^{2.g}$ | $R^{2.1.a}$ | $R^{2.1.1.a}$ | $R^{2.2.a}$ | — |
| 26 | $R^{2.g}$ | $R^{2.1.a}$ | $R^{2.1.1.b}$ | $R^{2.2.a}$ | — |
| 27 | $R^{2.g}$ | $R^{2.1.a}$ | $R^{2.1.1.c}$ | $R^{2.2.a}$ | — |
| 28 | $R^{2.h}$ | $R^{2.1.a}$ | $R^{2.1.1.a}$ | $R^{2.2.a}$ | — |
| 29 | $R^{2.h}$ | $R^{2.1.a}$ | $R^{2.1.1.b}$ | $R^{2.2.a}$ | — |
| 30 | $R^{2.h}$ | $R^{2.1.a}$ | $R^{2.1.1.c}$ | $R^{2.2.a}$ | — |
| 31 | $R^{2.e}$ | $R^{2.1.a}$ | $R^{2.1.1.c}$ | — | $R^{2.3.a}$ |
| 32 | $R^{2.e}$ | $R^{2.1.a}$ | $R^{2.1.1.c}$ | — | $R^{2.4.a}$ |
| 33 | $R^{2.e}$ | $R^{2.1.a}$ | $R^{2.1.1.c}$ | — | $R^{2.5.a}$ |
| 34 | $R^{2.g}$ | $R^{2.1.a}$ | $R^{2.1.1.c}$ | — | $R^{2.3.a}$ |
| 35 | $R^{2.g}$ | $R^{2.1.a}$ | $R^{2.1.1.c}$ | — | $R^{2.4.a}$ |
| 36 | $R^{2.g}$ | $R^{2.1.a}$ | $R^{2.1.1.c}$ | — | $R^{2.5.a}$ |
| 37 | $R^{2.h}$ | $R^{2.1.a}$ | $R^{2.1.1.c}$ | — | $R^{2.3.a}$ |
| 38 | $R^{2.h}$ | $R^{2.1.a}$ | $R^{2.1.1.c}$ | — | $R^{2.4.a}$ |
| 39 | $R^{2.h}$ | $R^{2.1.a}$ | $R^{2.1.1.c}$ | — | $R^{2.5.a}$ |
| 40 | $R^{2.i}$ | $R^{2.1.a}$ | $R^{2.1.1.a}$ | $R^{2.2.a}$ | — |
| 41 | $R^{2.i}$ | $R^{2.1.a}$ | $R^{2.1.1.b}$ | $R^{2.2.a}$ | — |
| 42 | $R^{2.i}$ | $R^{2.1.a}$ | $R^{2.1.1.c}$ | $R^{2.2.a}$ | — |
| 43 | $R^{2.j}$ | $R^{2.1.a}$ | $R^{2.1.1.a}$ | $R^{2.2.a}$ | — |

TABLE 1-continued

| E# | $R^2$ | $R^{2.1}$ | $R^{2.1.1}$ | $R^{2.2}$ | $R^{2.3-5}$ |
|---|---|---|---|---|---|
| 44 | $R^{2.j}$ | $R^{2.1.a}$ | $R^{2.1.1.b}$ | $R^{2.2.a}$ | — |
| 45 | $R^{2.j}$ | $R^{2.1.a}$ | $R^{2.1.1.c}$ | $R^{2.2.a}$ | — |
| 46 | $R^{2.k}$ | $R^{2.1.a}$ | $R^{2.1.1.a}$ | $R^{2.2.a}$ | — |
| 47 | $R^{2.k}$ | $R^{2.1.a}$ | $R^{2.1.1.b}$ | $R^{2.2.a}$ | — |
| 48 | $R^{2.k}$ | $R^{2.1.a}$ | $R^{2.1.1.c}$ | $R^{2.2.a}$ | — |
| 49 | $R^{2.l}$ | $R^{2.1.a}$ | $R^{2.1.1.a}$ | $R^{2.2.a}$ | — |
| 50 | $R^{2.l}$ | $R^{2.1.a}$ | $R^{2.1.1.b}$ | $R^{2.2.a}$ | — |
| 51 | $R^{2.l}$ | $R^{2.1.a}$ | $R^{2.1.1.c}$ | $R^{2.2.a}$ | — |

For a better understanding of the Table 1 $R^2$—Embodiments of the invention example (E#) 21, can also be read as a group $R^2$, wherein
$R^2$ is $R^{2.e}$ and $R^{2.e}$ is $C_{5\ or\ 6}$-heteroaryl-, containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; and
$R^{2.1}$ is $R^{2.1.a}$ and $R^{2.1.a}$ is selected from among H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and
$R^{2.1.1}$ is $R^{2.1.1.c}$ and $R^{2.1.1.c}$ is phenyl or selected from among

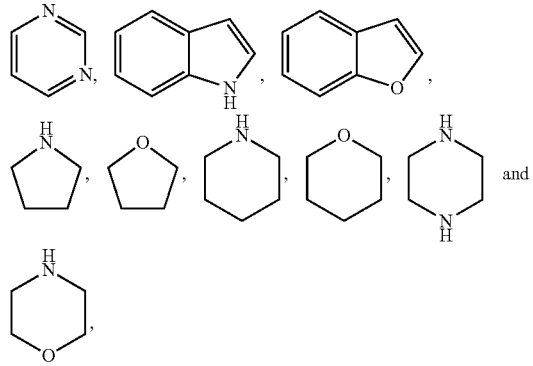

wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and
$R^{2.1.1.1}$ is independently selected from among F, Cl, Me, MeO— and cyclopropyl-; and
$R^{2.1.1.2}$ is independently selected from among Me, tetrahydrofuranylmethyl- and tetrahydropyranylmethyl; and
$R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

Preferred are the above compounds of formula 1, wherein $R^3$ is $R^{3.a}$ and $R^{3.a}$ is H.
Preferred are the above compounds of formula 1, wherein $R^3$ is $R^{3.b}$ and $R^{3.b}$ is F.
Preferred are the above compounds of formula 1, wherein $R^4$ is $R^{4.a}$ and $R^{4.a}$ is H, F, Cl, phenyl-H$_2$C—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—.
Preferred are the above compounds of formula 1, wherein $R^4$ is $R^{4.b}$ and $R^{4.b}$ is H or F.
Preferred are the above compounds of formula 1, wherein $R^4$ is $R^{4.c}$ and $R^{4.c}$ is F; preferably in ortho position.
Preferred are the above compounds of formula 1, wherein A is $A^a$ and $A^a$ is a bond or independently selected from among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$—, —($R^5$)(O)S═N—, —($R^5$N═)(O)S— and —N═(O)($R^5$)S—, and $R^5$ is $R^{5.a}$ and $R^{5.a}$ is independently selected from among H, $C_{1-4}$-alkyl- and NC—.
Preferred is a compound of formula 1, wherein
$R^{2.1}$ is $R^{2.1.a}$ and $R^{2.1.a}$ is selected from among H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and
$R^{2.1.1}$ is $R^{2.1.1.a}$ and $R^{2.1.1.a}$ is selected from among
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
$R^{2.1.1.1}$ is independently selected from among halogen, HO—, O═, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and
$R^{2.1.1.2}$ is independently selected from among O═, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.
Preferred is a compound of formula 1, wherein $R^2$ is $R^{2.d}$ and $R^{2.d}$ is phenyl; optionally substituted with one, two or three residues independently selected from $R^{2.1}$ and
$R^{2.1}$ is $R^{2.1.a}$ and $R^{2.1.a}$ is selected from among H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$- alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

Preferred is a compound of formula 1, wherein $R^1$ is independently selected from among H, $C_{1-4}$-alkyl-, halogen, HO—, $C_{1-4}$-alkyl-O—, $H_2N$—, $C_{1-6}$-alkyl-HN—, ($C_{1-6}$-alkyl)$_2$N— and $C_{1-6}$-alkyl-C(O)HN—;

or two $R^1$ are together $C_{1-4}$-alkylene;

$R^2$ is selected of the examples of the Table 1 $R^2$—Embodiments of the invention; preferably examples (E#) 7-51, preferably one of the groups selected from among 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50— and 51;

$R^3$ is H or F;

$R^4$ is independently selected from among halogen, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=) S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from among H, $C_{1-6}$-alkyl- and NC—;

or a salt thereof.

Preferred is a compound of formula 1, wherein $R^1$ is $R^{1.a}$ and $R^{1.a}$ is independently selected from among H, $C_{1-4}$-alkyl-, F— and HO—.

or two $R^1$ are together $C_{1-4}$-alkylene;

$R^2$ is selected of the examples of the Table 1 $R^2$—Embodiments of the invention; preferably examples (E#) 7-51, preferably one of the groups selected from among 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50— and 51;

$R^3$ is H, F;

$R^4$ is $R^{4.a}$ and $R^{4.a}$ is H, F, Cl, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=) S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from among H, $C_{1-6}$-alkyl- and NC—;

or a salt thereof.

Preferred is a compound of formula 1, wherein $R^1$ is $R^{1.a}$ and $R^{1.a}$ is independently selected from among H, $C_{1-4}$-alkyl-, F— and HO—.

or two $R^1$ are together $C_{1-4}$-alkylene;

$R^2$ is selected of the examples of the Table 1 $R^2$—Embodiments of the invention; preferably examples (E#) 7-51, preferably one of the groups selected from among 13, 14, 15, 16, 17, 18 or 25, 26, 27, 28, 29, 30, 34, 35, 36, 37, 38, 39 or 43, 44, 45, 46, 47— and 48;

$R^3$ is H or F;

$R^4$ is $R^{4.a}$ and $R^{4.a}$ is H, F, Cl, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—;

A is $A^a$ and $A^a$ is a bond or independently selected from
among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from among H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —$CH_2$—;

$R^2$ is selected of the examples of the Table 1 $R^2$—Embodiments of the invention; preferably examples (E#) 7-51, preferably one of the groups selected from among 13, 14, 15, 16, 17, 18 or 25, 26, 27, 28, 29, 30, 34, 35, 36, 37, 38, 39 or 43, 44, 45, 46, 47— and 48;

$R^3$ is H or F;

$R^4$ is $R^{4.b}$ and $R^{4.b}$ is H or F;

A is $A^a$ and $A^a$ is a bond or independently selected from
among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from among H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —$CH_2$—;

$R^2$ is selected of the examples of the Table 1 $R^2$—Embodiments of the invention; preferably examples (E#) 7-51, preferably one of the groups selected from among 13-15, 16-18 or 25-30, 34-39— and 43-48;

$R^3$ is H or F;

$R^4$ is $R^{4.b}$ and $R^{4.b}$ is H or F;

A is $A^a$ and $A^a$ is a bond or independently selected from among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from among H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —CH$_2$—;

$R^2$ is selected from among $R^{2.1}$;

phenyl-; optionally substituted with one or two residues independently selected from $R^{2.1}$; optionally substituted with one $R^{2.3}$;

$C_5$-heteroaryl-; containing two or three independently selected from among S, O and N, wherein carbon atoms of the ring are optionally and independently from each other substituted with one $R^{2.1}$; wherein nitrogen atoms of the ring are optionally and independently from each other substituted with one $R^{2.2}$;

monocyclic $C_6$-heterocyclyl containing one or two nitrogen atoms, wherein the ring is fully or partially saturated, wherein carbon atoms of the ring are optionally and independently from each other substituted with one $R^{2.1}$; wherein nitrogen atoms of the ring are optionally and independently from each other substituted with one $R^{2.2}$; and bicyclic $C_{9\ or\ 10}$-heterocyclyl-; containing one, two, three or four heteroatoms independently selected from among S(O)$_2$, O and N, wherein the ring is fully or partially saturated, wherein carbon atoms of the ring are optionally and independently from each other substituted with one, two or three $R^{2.1}$; wherein nitrogen atoms of the ring are optionally and independently from each other substituted with one $R^{2.2}$;

$R^{2.1}$ is independently selected from among halogen, NC—, O=, H-A-,

H-A-$C_{1-4}$-alkylene-, $R^{2.1.1}$-A-, $C_{1-4}$-alkyl-A-, $C_{3-6}$-cycloalkyl-A-, $R^{2.1.1}$—$C_{1-4}$-alkylene-A-, $C_{1-4}$-alkyl-A-$C_{1-4}$-alkylene-, HO—$C_{1-4}$-alkylene-A-$C_{1-4}$-alkylene-; preferably F, NC—, O=, H-A-, H-A-CH$_2$—, $R^{2.1.1}$-A-, H$_3$C-A-, H$_3$C—CH$_2$-A-, Cyclopropyl-A-, $R^{2.1.1}$—CH$_2$—CH$_2$-A-, $R^{2.1.1}$—CH$_2$-A-, H$_3$C-A-CH$_2$—CH$_2$— and HO—$C_4$-alkylene-A-CH$_2$—;

$R^{2.1.1}$ is independently selected from among phenyl-; and $C_{5\ or\ 6}$-heterocyclyl-; containing one or two heteroatoms independently selected from among O and N, wherein the ring is fully or partially saturated, wherein nitrogen atoms of the ring are optionally and independently from each other substituted with one $C_{1-4}$-alkyl-; preferably H$_3$C—;

$R^{2.2}$ is independently selected from among H-A-$C_{1-4}$-alkylene-, $C_{3-6}$-cycloalkyl-, $C_{1-4}$-alkyl-A-$C_{1-4}$-alkylene-, $R^{2.1.1}$-A-$C_{1-4}$-alkylene-, $C_{1-4}$-alkyl-C(O)—; preferably H-A-CH$_2$—, H-A-CH$_2$—CH$_2$—, cyclopropyl-, H$_3$C-A-CH$_2$—CH$_2$—, $R^{2.1.1}$-A-CH$_2$— and H$_3$C—C(O)—;

$R^{2.3}$ and $R^4$ are together a group selected from among —N($R^{2.3.1}$)—, —C(O)N($R^{2.3.2}$)— and —N($R^{2.3.1}$)C(O)—;

$R^{2.3.1}$ is independently selected from among H— and H$_3$C—;

$R^3$ is H or F;

$R^4$ is $R^{4.b}$ and $R^{4.b}$ is H or F;

A is a bond or independently selected from among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$— and —N=(O)($R^5$)S—;

$R^5$ is independently selected from among H— and $C_{1-4}$-alkyl-;

or a salt thereof.

Particularly preferred are the above compounds of formula 1, wherein $R^3$ is H and $R^4$ is F.

Particularly preferred are the above compounds of formula 1, wherein $R^3$ is H and $R^4$ is H.

Preferred are the above compounds of formula 1, wherein $R^2$ is $R^{2.r}$ and $R^{2.r}$ is selected from among the substituents (a1) to (g1) particularly preferred (a1) and (b1),

(a1)

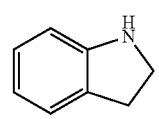

(b1)

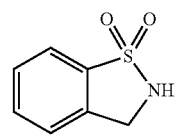

(c1)

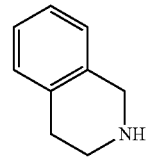

(d1)

(e1)

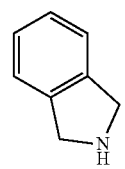

(f1)

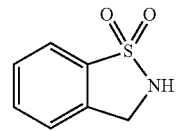

(g1)

wherein carbon atoms of the rings are optionally and independently from each other substituted with one, two or three $R^{2.1}$; wherein a nitrogen atom of the ring is optionally substituted with $R^{2.2}$.

Preferred are the above compounds of formula 1, wherein $R^2$ is $R^{2.r}$ and $R^{2.r}$ is selected from among the substituents (a2) to (g2)

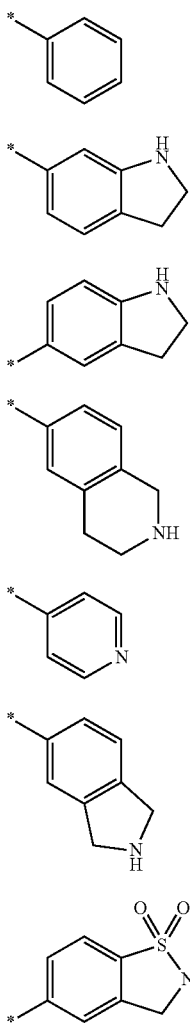

(a2)

(b2)

(c2)

(d2)

(e2)

(f2)

(g2)

wherein carbon atoms of the rings are optionally and independently from each other substituted with one, two or three $R^{2.1}$; wherein a nitrogen atom of the ring is optionally substituted with $R^{2.2}$.

Preferred are the above compounds of formula 1, wherein $R^2$ is $R^{2.r}$ and $R^{2.r}$ is selected from among the substituents (a2) and (b2)

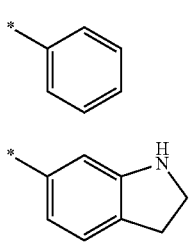

(a2)

(b2)

wherein carbon atoms of the ring are optionally and independently from each other substituted with one, two or three $R^{2.1}$; preferably one or two, wherein the nitrogen atom of the ring are optionally substituted with $R^{2.2}$.

Preferably $R^{2.1}$ denotes a group selected from among —CN, F, —SO$_2$—C$_{1-2}$-alkyl, =O, —CH$_3$, —NH—SO$_2$—CH$_3$, —SO$_2$—NH$_2$, —CONH$_2$, and —C$_2$H$_5$—O—CH$_3$.

Preferably $R^{2.2}$ denotes —CH$_3$.

Particularly preferred $R^{2.1}$ denotes a group selected from among —CN, F, —SO$_2$—C$_{1-2}$-alkyl, =O, —CH$_3$, —NH—SO$_2$—CH$_3$, —SO$_2$—NH$_2$, —CONH$_2$, and —C$_2$H$_5$—O—CH$_3$, and $R^{2.2}$ denotes —CH$_3$.

Preferred are the above compounds of formula 1, wherein $R^2$ is $R^{2.s}$ and $R^{2.s}$ is selected from among the substituents (a3) and (b3)

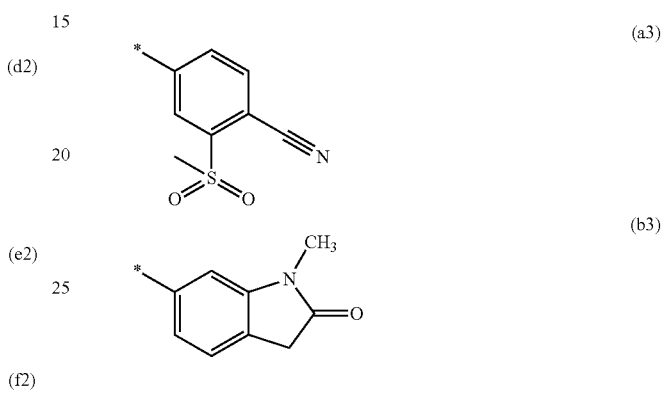

(a3)

(b3)

Preferred are the compounds of formula 1, wherein the compounds are selected from the group consisting of examples 1 and 4.

Preferred are the above compounds of formula 1, in its enantiomerically pure form of formula 1'

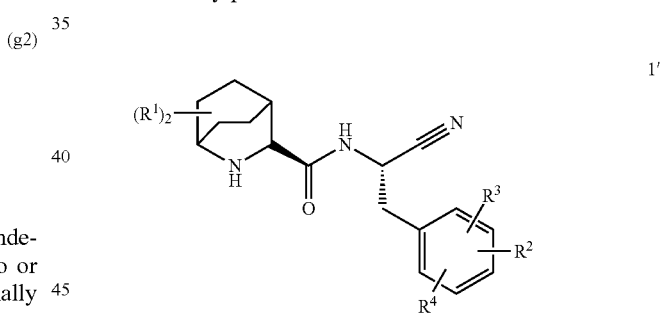

1' wherein $R^1$, $R^2$, $R^3$ and $R^4$ have the above mentioned meaning.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, H$_2$N, S(O), S(O)$_2$, NC (cyano), HOOC, F$_3$C or the like, the skilled artisan can see the radical attachment point(s) to the molecule from the free valences of the group itself. For combined groups comprising two or more subgroups, the last named subgroup is the radical attachment point, for example, the substituent "aryl-$C_{1-4}$-alkyl-" means an aryl group which is bound to a $C_{1-4}$-alkyl-group, the latter of which is bound to the core or to the group to which the substituent is attached.

Alternatively "*" indicates within a chemical entity the binding site, i.e. the point of attachment In case a compound of the present invention is depicted in form of a chemical name and as a formula in case of any discrepancy the formula shall prevail. An asterisk is may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer selected from among 2, 3, 4, 5 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer selected from among 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH_2$—$CH(CH_3)$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{3-n}$-cycloalkyl", wherein n is an integer selected from among 4, 5, 6, 7 or 8, preferably 4, 5 or 6, either alone or in combination with another radical denotes a cyclic, saturated, unbranched hydrocarbon radical with 3 to 8 C atoms. For example the term $C_{3-8}$-cycloalkyl includes cyclopropyl, cyclobutyl, cyclopentyl, cyclohexyl, cycloheptyl, cyclooctyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC$—, $HF_2C$—, $F_3C$—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "$C_{5-10}$-heterocyclyl" means a saturated or unsaturated mono- or polycyclic-ring systems including aromatic ring system containing one or more heteroatoms independently selected from among N, O or $S(O)_r$, wherein r=0, 1 or 2, consisting of 5 to 10 ring atoms wherein none of the heteroatoms is part of the aromatic ring. The term "heterocyclyl" is intended to include all the possible isomeric forms. Thus, the term "heterocyclyl" includes the following exemplary structures which are not depicted as radicals as each form may be attached through a covalent (single or double) bond to any atom so long as appropriate valences are maintained:

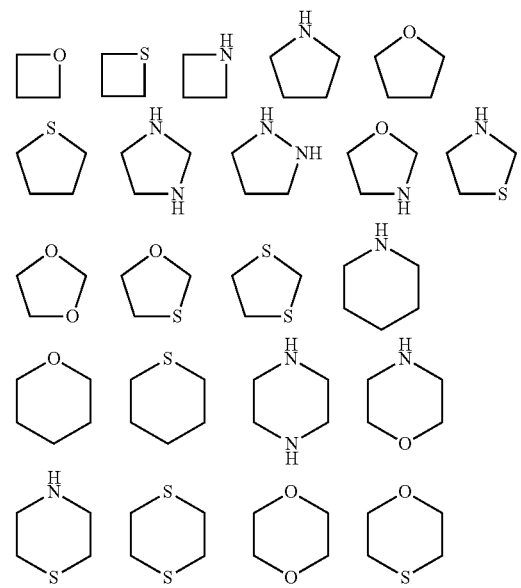

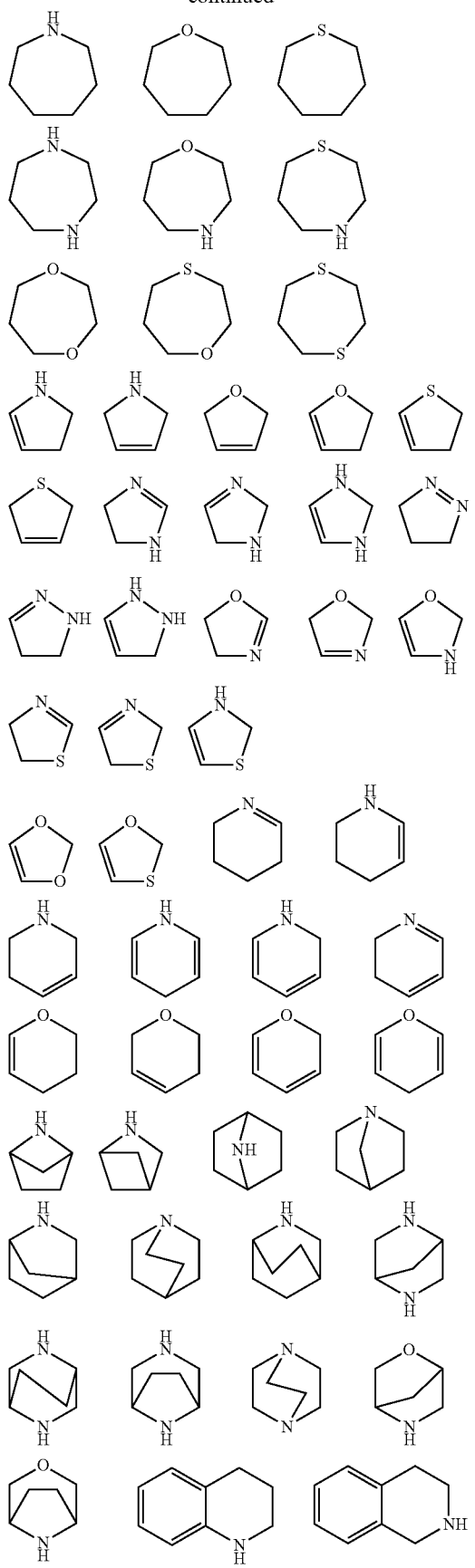

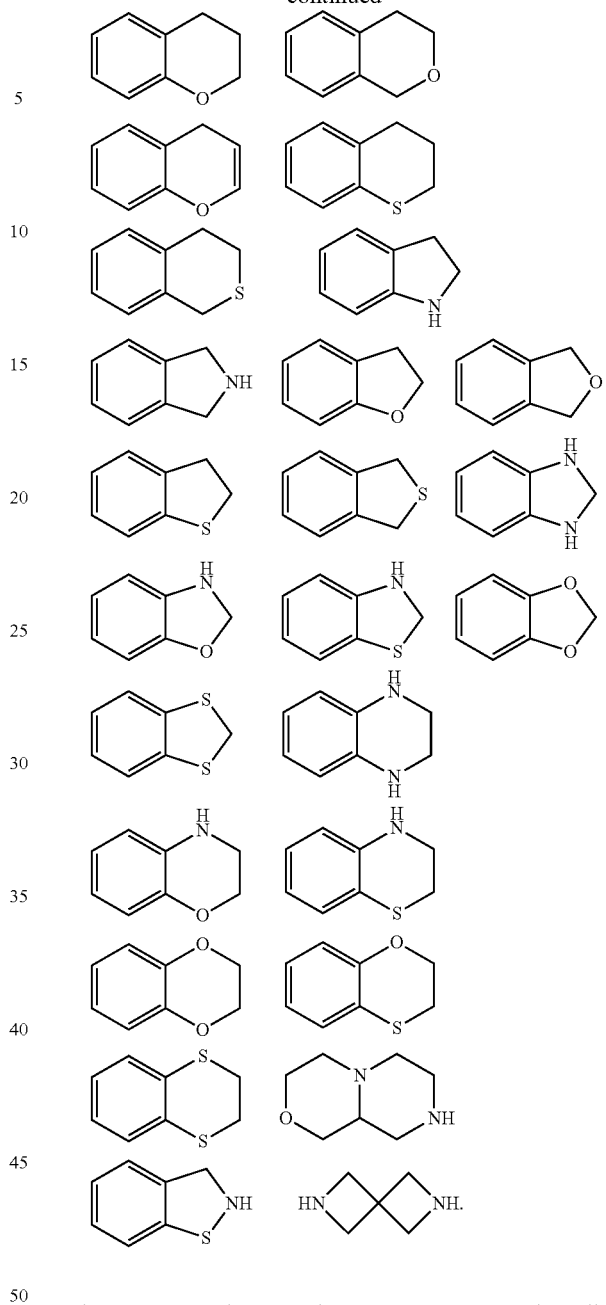

The term "$C_{5-10}$-heteroaryl" means a mono- or polycyclic-ring systems containing one or more heteroatoms independently selected from among N, O or $S(O)_r$, wherein r=0, 1 or 2, consisting of 5 to 10 ring atoms wherein at least one of the heteroatoms is part of aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

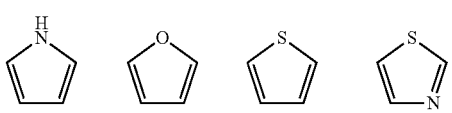

-continued

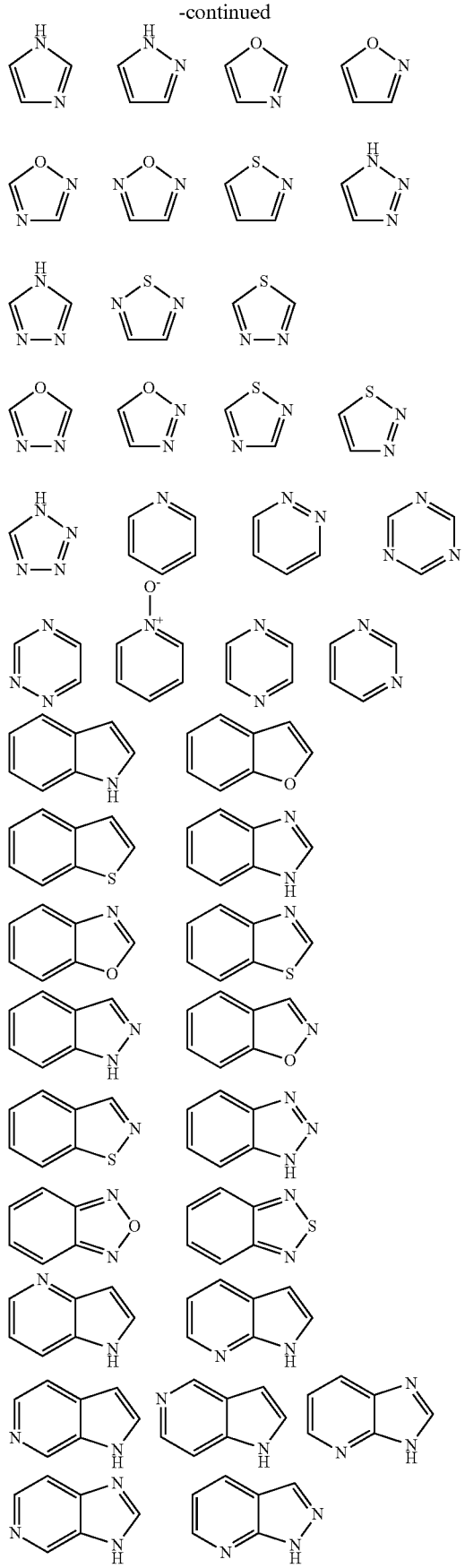

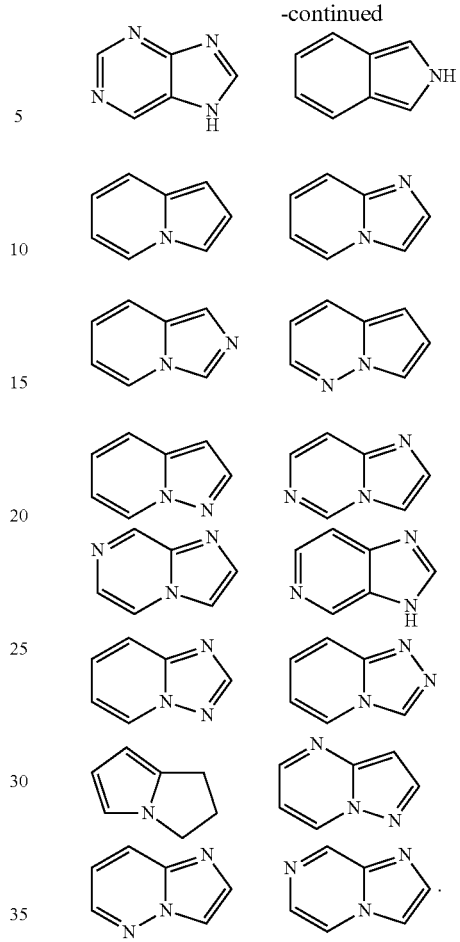

Preparation

General Synthetic Methods

The invention also provides processes for making a compound of Formula I. In all methods, unless to specified otherwise, $R^1$, $R^2$ and n in the formulas below shall have the meaning of $R^1$, $R^2$ and n in Formula I of the invention described herein above.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula V, VII and IX may be made by the method outlined in Scheme 1:

Scheme 1

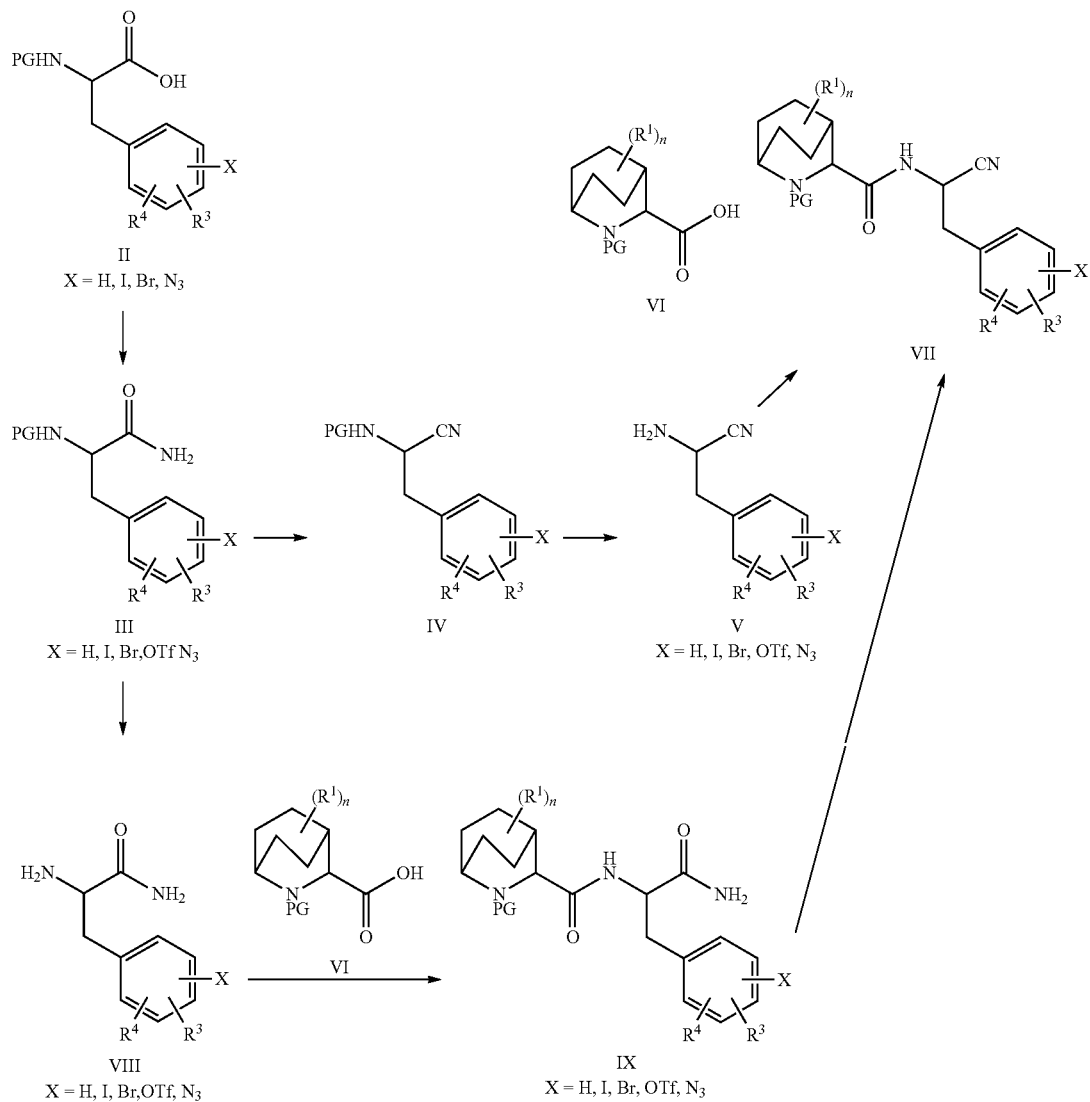

As illustrated in Scheme 1, a compound of Formula II, wherein PG represents a protecting group (e.g. tert-butoxycarbonyl), may be reacted with an aqueous ammonia solution, using standard literature procedures for the formation of an amide. For example, in the presence of a base such as N-methyl-morpholine or N-ethyl-morpholine and an activating agent such as O-(7-Azabenzotriazol-1-yl)-N,N,N',N'-tetramethyluronium hexafluorophosphate (HATU) or O-(Benzotriazol-1-yl)-N,N,N',N'-tetramethyluroniumtetrafluoroborate (TBTU). The reaction is conveniently carried out in a suitable solvent such as N,N-dimethylformamide. Standard peptide coupling reactions known in the art (see for example M. Bodanszky, 1984, The Practice of Peptide Synthesis, Springer-Verlag) may be employed in these syntheses.

Dehydration of an amide such as in a compound of Formula III or Formula IX to the corresponding nitrile of Formula IV or VII may be carried out by use of a dehydration agent such as (methoxycarbonylsulfamoyl)triethyl ammonium hydroxide, in a suitable solvent such as dichloromethane (DCM).

Reacting an acid of Formula VI using standard literature procedures for the formation of an amide, for example in the presence of a base such as N,N-diisopropylethylamine (DIPEA) and an activating agent such as HATU or TBTU, with an amine of Formula V or VIII in a suitable solvent, provides a compound of Formula VII or IX. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, trifluoroacetic acid, p-toluenesulfonic acid or HCl may be used in a suitable solvent such as water, DCM or dioxane. Another method to deprotect tert-butoxycarbonyl is the reaction with trimethyliodosilane or trimethylchlorosilane in combination with sodium iodide in an appropriate solvent like acetonitrile, DMF or DCM.

Scheme 2
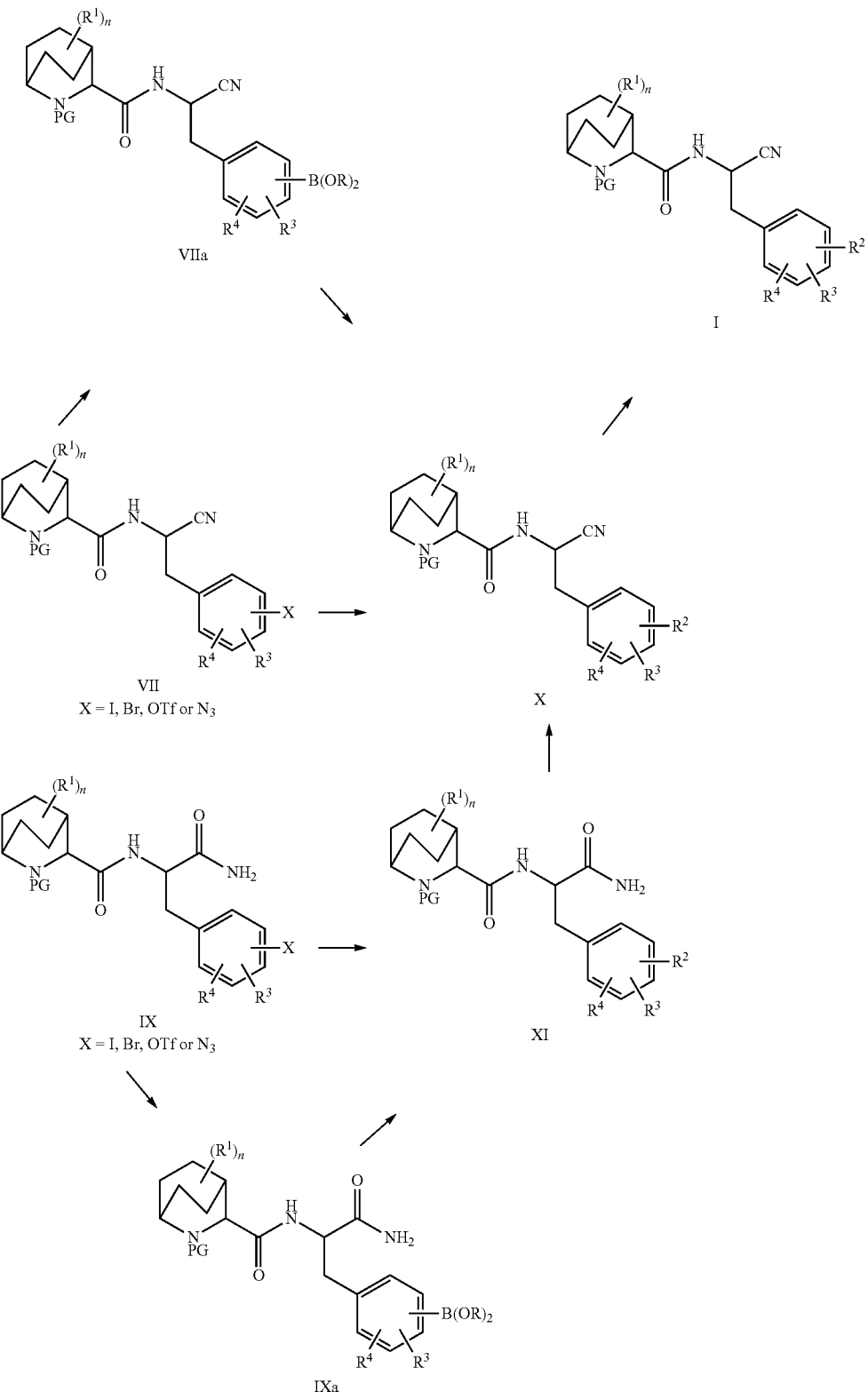
During the reaction sequences depicted in Scheme 1 and Scheme 2 a hydroxy group (X=OH) can be converted to a trifluoromethanesulfonyl group (X=OTf) at any level. Especially, a compound IX with X=OH is transformed to the appropriate triflate (X=OTf) by reaction with N,N-bis-(trifluoromethanesulfonyl) aniline, or trifluoromethanesulfonyl chloride or anhydride, in the presence of an organic base e.g. triethylamine, morpholine, piperidine, DIPEA in an appropriate anhydrous solvent, e.g. DCM.

As illustrated in Scheme 2, (transition) metal catalyzed reaction of a compound of Formula VII or IX wherein X is I, Br, Cl or OTf, provides a compound of Formula X or XI. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula X or XI. Alternatively, reaction of a compound of Formula VII or IX, wherein X is I, Br, Cl or OTf with a tributyl(vinyl)tin reagent in the presence of a suitable catalyst such as bis-(triphenylphosphin)-palladiumchloride, in a suitable solvent such as dimethylformamide (DMF) and if desireable in the presence of an additive such as tetraethylammonium chloride provides compounds of Formula X or XI. Further, reaction of a compound of Formula VII or IX, wherein X is I or Br, may be reacted with an amine in the presence of a suitable catalyst such as Cu(I)I and a suitable base such as caesium carbonate and a suitable promotor such as L-proline provides a compound of Formula X or XI.

In an inversed fashion compounds of formula VII or IX (X: I, Br, Cl, OTf) can be converted into the corresponding boronic acid derivatives VIIa or IXa, wherein R can be H or lower alkyl independently and the residues R can form a ring. For example, VII or IX can be reacted with bis-pinacolato-diboron in the presence of a suitable catalyst such as 1,1-bis(di-tert-butylphosphino)ferrocene palladium dichloride and a suitable base such as potassium acetate or sodium, potassium or cesium carbonate or phosphate, in a suitable solvent such as dioxan, dimethylformamide (DMF), or dichloromethane (DCM) to yield the boronic esters VIIa or IXa, respectively. These can be reacted with appropriate aromatic halides in analogy as above to yield the desired coupling products of formula X or XI.

Further, as illustrated in Scheme 2, reaction of a compound of Formula VII or IX, wherein X is $N_3$ with an alkyne in the presence of a suitable catalyst such as copper(II)sulfate pentahydrate and a suitable reducing agent such as L-ascorbic acid in a suitable solvent such as dimethyl sulfoxide (DMSO)/water provides a compound of Formula X or XI.

Further modifications of compounds of Formula X, XI and I by methods known in the art and illustrated in the Examples below, may be used to prepare additional compounds of the invention. Dehydration of an amide of Formula XI to the corresponding nitrile of Formula X may be carried out by use of a dehydration agent such as (methoxycarbonylsulfamoyl) triethyl ammonium hydroxide, in a suitable solvent such as DCM.

Scheme 3

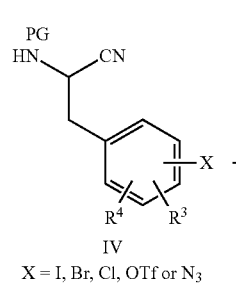

IV
X = I, Br, Cl, OTf or $N_3$

-continued

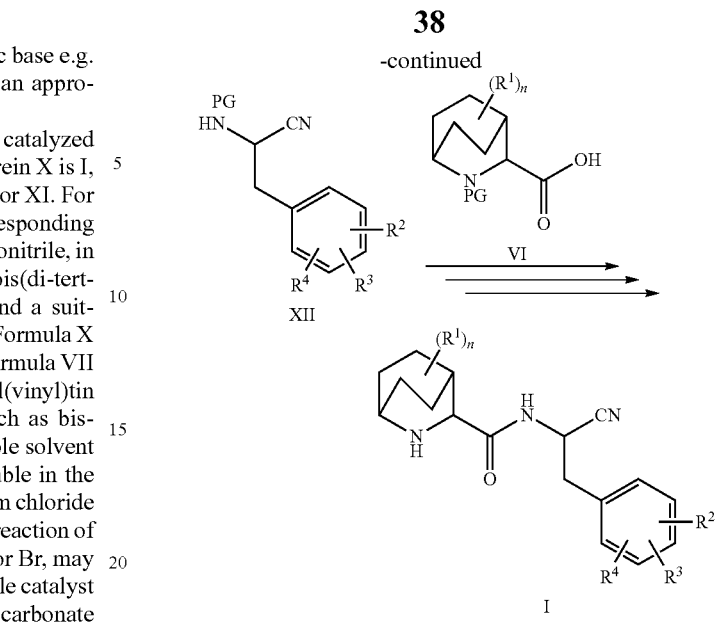

As illustrated in Scheme 3, (transition) metal catalyzed reaction of a compound of Formula IV wherein X is I, Br, cl or OTf provides a compound of Formula XII. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula XII.

An acid of Formula VI using standard literature procedures for the formation of an amide, for example in the presence of a base such as DIPEA and an activating agent such as HATU or TBTU, can be reacted with an amine of Formula XII in a suitable solvent. Standard peptide coupling reactions known in the art (see for example M. Bodanszky, 1984, The Practice of Peptide Synthesis, Springer-Verlag) may be employed in these syntheses. Deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, p-toluenesulfonic acid, trifluoroacetic acid or HCl may be used in a suitable solvent such as water, DCM or dioxane and can be performed on the crude amide coupling product to provide a compound of Formula I. Another method to deprotect tert-butoxycarbonyl is the reaction with trimethyliodosilane or trimethylchlorosilane in combination with sodium iodide in an appropriate solvent like acetonitrile, DMF or DCM.

SYNTHETIC EXAMPLES

The following are representative compounds of the invention which can be made by the general synthetic schemes, the examples, and known methods in the art. Starting materials and intermediates were either commercially available and purchased from catalogues of ABCR, ACROS, ACTIVATE, AK SCIENTIFIC LABS, ALDRICH, ALFA, ALLICHEM, APOLLO, ARKPHARMINC, AROMACIRCLE, BACHEM, COMBI-BLOCKS, COMBI-PHOS, ENAMINE, FLUKA, FRONTIER SCIENTIFIC, J. T BAKER, MERCACHEM, MERCK, NETCHEM, RIEDEL DE HAEN or were synthesized according to literature or as described below in "Synthesis of starting materials/educts" Liquid chromatography-mass spectroscopy (LCMS) retention time and observed m/z data for the compounds below are obtained by one of the following methods:

LC-MS Method 001_CA04

| Device-Description | Agilent 1100 with DAD, CTC Autosampler and Waters MSD |
|---|---|
| Column | Waters XBridge C18 |
| Column Dimension | 4.6 × 30 mm |
| Particle Size | 3.5 μm |

| Gradient/Solvent Time [min] | % Sol [H2O 0.1% NH4OH] | % Sol [Methanol] | Flow [ml/min] | Temp [° C.] |
|---|---|---|---|---|
| 0.0 | 80.0 | 20.0 | 2.0 | 60.0 |
| 1.7 | 0.0 | 100.0 | 2.0 | 60.0 |
| 2.5 | 0.0 | 100.0 | 2.0 | 60.0 |

LC-MS Method 004_CA01

| Device-Description | Agilent 1100 with DAD, Waters Autosampler and MSD |
|---|---|
| Column | Waters Sunfire C18 |
| Column Dimension | 4.6 × 30 mm |
| Particle Size | 3.5 μm |

| Solvent Gradient time [min] | % Sol [H$_2$O 0.1% TFA] | % Sol [Acetonitril] | Flow [ml/min] | Temp [° C.] |
|---|---|---|---|---|
| 0.0 | 98.0 | 2.0 | 2.5 | 60.0 |
| 1.5 | 0.0 | 100.0 | 2.5 | 60.0 |
| 1.8 | 0.0 | 100.0 | 2.5 | 60.0 |

LC-MS Method V001_003

| Device-Description | Waters Alliance with DAD and MSD |
|---|---|
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 4 | 60 |
| 0.20 | 95 | 5 | 4 | 60 |
| 1.5 | 0 | 100 | 4 | 60 |
| 1.75 | 0 | 100 | 4 | 60 |

LC-MS Method V001_007

| Device-Description | Waters Alliance with DAD and MSD |
|---|---|
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

LC-MS Method V002_005

| Device-Description | Waters Alliance with DAD and MSD |
|---|---|
| Column | Waters Sunfire C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

LC-MS Method V003_003

| Device-Description | Waters Alliance with DAD and MSD |
|---|---|
| Column | Waters XBridge C18 |
| Column Dimension | 4.6 × 30 mm |
| Particle Size | 3.5 μm |

| Solvent Gradient time [min] | % Sol [H$_2$O, 0.1% NH$_3$] | % Sol [Acetonitril] | Flow [ml/min] | Temp [° C.] |
|---|---|---|---|---|
| 0.0 | 95 | 5 | 4 | 60 |
| 0.2 | 95 | 5 | 4 | 60 |
| 1.5 | 0 | 100.0 | 4 | 60 |
| 1.75 | 0 | 100 | 4 | 60 |

LC-MS Method V011_S01

| Device-Description | Waters Alliance with DAD and MSD |
|---|---|
| Column | Waters XBridge C18 |
| Device-Description | Waters Alliance with DAD and MSD |
| Column Dimension | 4.6 × 30 mm |
| Particle Size | 3.5 μm |

| Solvent Gradient time [min] | % Sol [H$_2$O, 0.1% NH$_3$] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method V012_S01

| Device-Description | Waters Alliance with DAD and MSD |
|---|---|
| Column | Waters XBridge C18 |
| Column Dimension | 4.6 × 30 mm |
| Particle Size | 3.5 μm |

| Solvent Gradient time [min] | % Sol [H$_2$O, 0.1% TFA] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method V018_S01

| Device-Description | Waters Alliance with DAD and MSD |
|---|---|
| Column | Waters Sunfire C18 |
| Column Dimension | 4.6 × 30 mm |
| Particle Size | 3.5 μm |

| Solvent Gradient time [min] | % Sol [H$_2$O, 0.1% TFA] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method W018_S01

| Device Description | Waters 1525 with DAD and MSD |
|---|---|
| Column: | Waters Sunfire C18 |
| Column Dimension | 4.6 × 30 mm |
| Particle Size | 2.5 μm |

| Gradient/Solvent Time [min] | % Sol [H2O, 0.1% TFA] | % Sol [ACN] | Flow [ml/min] | Temp [° C.] |
|---|---|---|---|---|
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

LC-MS Method X001_004

| Device-Description | Waters Acquity with DAD and MSD |
|---|---|
| Column | Waters XBridge C18 |
| Column Dimension | 2.1 × 20 mm |
| Particle Size | 2.5 μm |

| Gradient/Solvent Time [min] | % Sol [H$_2$O, 0.10% TFA] | % Sol [Methanol] | Flow [ml/min] | Temp [° C.] |
|---|---|---|---|---|
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

LC-MS Method X012_S01

| Device-Description | Waters Acquity with DAD and MSD |
|---|---|
| Column | Waters XBridge BEH C18 |
| Column Dimension | 2.1 × 30 mm |
| Particle Size | 1.7 μm |

| Solvent Gradient time [min] | % Sol [H$_2$O, 0.1% TFA] | % Sol [Acetonitril] | Flow [ml/min] | Temp [° C] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

LC-MS Method X018_S01

| Device-Description | Waters Acquity with DAD and MSD |
|---|---|
| Column | Waters Sunfire C18 |
| Column Dimension | 2.1 × 30 mm |
| Particle Size | 2.5 μm |

| Gradient/Solvent Time [min] | % Sol [H$_2$O, 0.1% TFA] | % Sol [Acetonitril] | Flow [ml/min] | Temp [° C.] |
|---|---|---|---|---|
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

LC-MS Method Z002_005

| Device Description | Agilent 1200 with DAD and MSD |
|---|---|
| Column: | Waters Sunfire C18 |
| Column Dimension | 3 × 30 mm |
| Particle Size | 2.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

LC-MS Method Z011_S03

| Device-Description | Agilent 1200 with DAD and MSD |
|---|---|
| Column | Waters XBridge C18 |
| Column Dimension | 3 × 30 mm |
| Particle Size | 2.5 μm |

| Gradient/Solvent Time [min] | % Sol [H$_2$O, 0.1% NH3] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z012_S04

| Device-Description | Agilent 1200 with DAD and MSD |
|---|---|
| Column | Waters XBridge C18 |
| Column Dimension | 3 × 30 mm |
| Particle Size | 2.5 μm |

| Solvent Gradient time [min] | % Sol [H$_2$O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z018_S04
| Device-Description | Agilent 1200 with DAD and MSD | | | |
|---|---|---|---|---|
| Column | Waters Sunfire C18 | | | |
| Column Dimension | 3 × 30 mm | | | |
| Particle Size | 2.5 μm | | | |
| Solvent Gradient time [min] | % Sol [H$_2$O, 0.1% TFA] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |
Method A
Synthesis of (2S)—N-[(1S)-1-cyano-2-[4-(4-cyano-3-methylsulfonyl-phenyl)-2-fluoro-phenyl]ethyl]-3-azabicyclo[2.2.2]octane-2-carboxamide (Example 1)
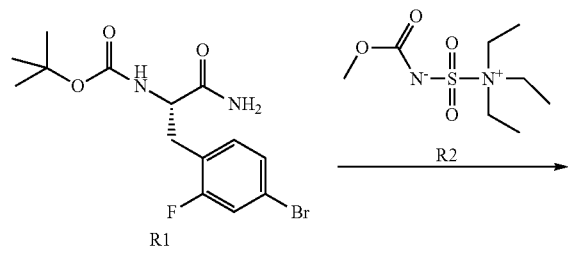
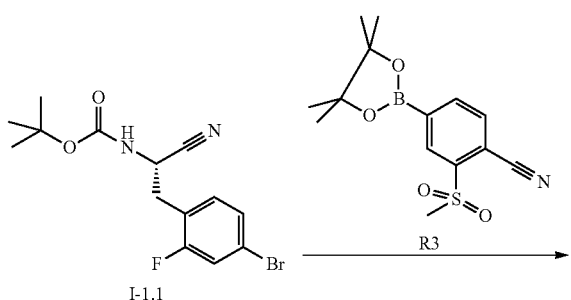
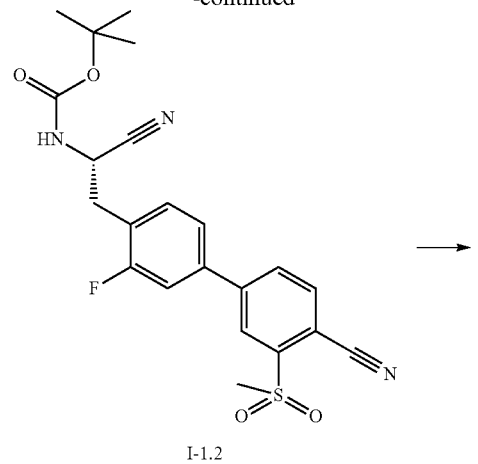
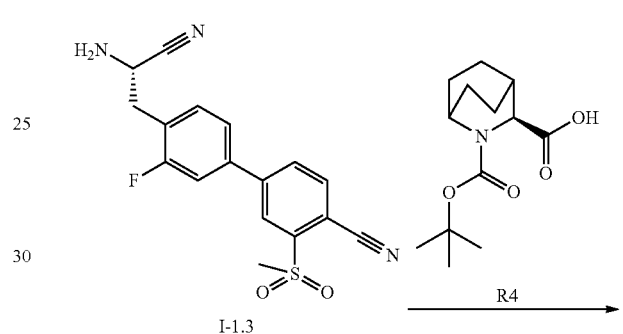
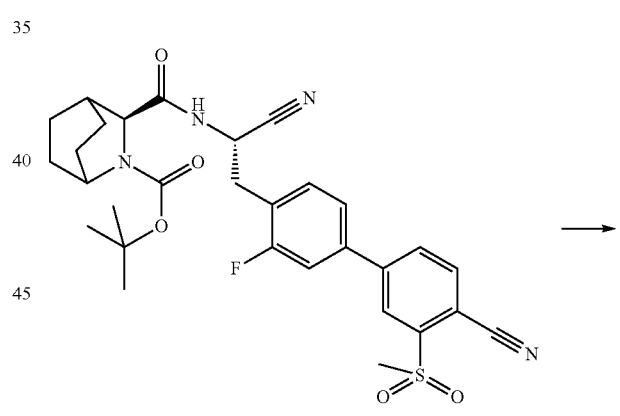
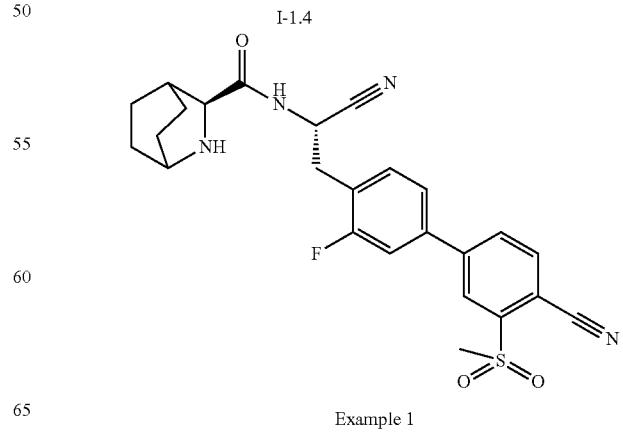

Step 1: Synthesis of Intermediate I-1.1

R1 (20.0 g, 55.4 mmol) is suspended in DCM (400 mL) and R2 (26.4 g, 110.9 mmol) is added. The reaction mixture is stirred for 12 h under argon atmosphere. Afterwards the reaction mixture is washed with water. The organic layer is dried over MgSO$_4$, filtrated and the filtrate is concentrated. The residue is dissolved in DCM, filtrated by flash chromatography (using solvent mixture cyclohexane/ethyl acetate=70/30) and the filtrate is concentrated. Yield 97% m/z 287/343 [M+H]+, rt 1.29 min, LC-MS Method X012_S01.

The following intermediates as shown in Table 2 are synthesized in a similar fashion from the appropriate intermediate or by direct boronylation of Intermediate I-1.1:

MgSO$_4$. After filtration the solution is evaporated in vacuo. The residue is dissolved in DCM and purified by MPLC (cyclohexane/ethyl acetate 8:2, wave length 230 nm). The fractions containing the product are combined and evaporated in vacuo. Yield 97% m/z 391 [M+H]+, rt 1.36 min, LC-MS Method V012_S01.

Step 2: Synthesis of Intermediate I-1.2

To I-1.1 (3.00 g, 8.74 mmol) in acetonitrile (50 mL) R3 (2.82 g, 9.18 mmol) and potassium phosphate solution (2 mol/L, 8.74 mL) are added. The mixture is purged with argon, [1,1'-Bis(di-tert-butylphosphino)ferrocene]palladium dichloride (0.57 g, 0.87 mmol) is added and then the reaction

TABLE 2

| Intermediate | Structure | m/z [M + H]+ | rt (min) | LC-MS method |
|---|---|---|---|---|
| I-1.1.1 | 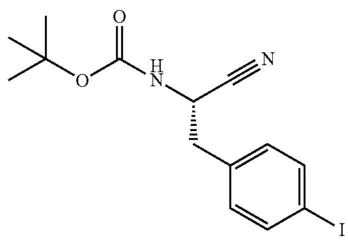 [SMILES: CC(C)(C)OC(=O)N[C@H](C#N)Cc1ccc(I)cc1] | 395 [M + Na]+ | 1.43 | V001_007 |
| I-1.1.2 | 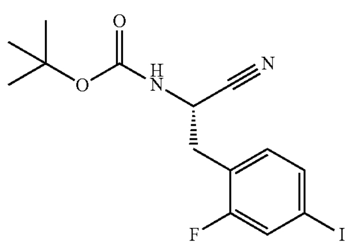 [SMILES: CC(C)(C)OC(=O)N[C@H](C#N)Cc1ccc(I)cc1F] | 391 | 1.29 | V012_S01 |
| I-1.1.3 | 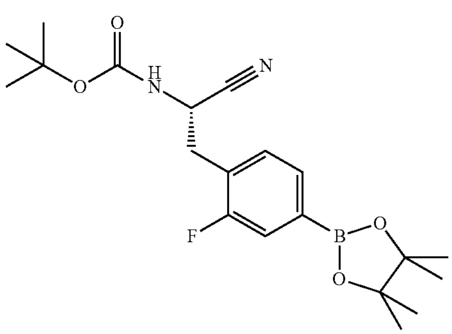 [SMILES: CC(C)(C)OC(=O)N[C@H](C#N)Cc1ccc(B2OC(C)(C)C(C)(C)O2)cc1F] | 391 | 1.36 | V012_S01 |

Step 1a: Synthesis of Intermediate I-1.1.3

Intermediate I-1.1 (5.8 g, 16.9 mmol), bis-pinacolato-diboron (5.2 g, 20.28 mmol), potassium acetate (4.976 g, 50.7 mmol) and Bis(diphenylphosphino)ferrocene]dichloropalladium(II) (PdCl2(dppf)) as DCM complex (1.38 g, 1.69 mmol) are suspended in dioxane under argon and stirred for 2 h at 80° C. After cooling the mixture is treated with DCM and filtered. The filtrate is washed with water and dried over mixture is heated to 80° C. for 2.5 h. Ethyl acetate and half saturated brine are added to the reaction mixture. The organic layer is dried over MgSO$_4$ and concentrated. Yield 97% m/z 461/444 [M+NH4]+/[M+H]+, rt 1.12 min, LC-MS Method V011_S01.

The following intermediates as shown in Table 3 are synthesized in a similar fashion from the appropriate intermediate:

TABLE 3

| Intermediate | Educt | Structure of Intermediate | m/z [M + H]+ | rt (min) | LC-MS method |
|---|---|---|---|---|---|
| I-1.2.1 | I-1.1.3 | | 396 | 0.96 | V012_S01 |
| I-1.2.2 | I-1.1.1 | | 392 | 1.36 | V001_007 |
| I-1.2.3 | I-1.1.2 | | 444 | 1.21 | V018_S01 |
| I-1.2.4 | I-1.1.3 | | 446 | 1.18 | V012_S01 |

During the synthesis of intermediates I-1.2.1 and I-1.2.4 the bromide (I-1.1) is transformed into the corresponding dioxaborolane compound: To I-1.1 (5.80 g, 17 mmol) in anhydrous dioxane (60 mL) Bis(pinacolato)diboron (5.20 g, 20 mmol) and potassium acetate (4.98 g, 51 mmol) are added. The mixture is purged with argon, [1,1'-Bis(diphenylphosphino)ferrocene]dichloropalladium(II) (1.38 g, 1.7 mmol) is added to the mixture and heated to 80° C. for 2 h. DCM is added and the mixture is filtrated. The filtrate is diluted with water and extracted with DCM. The organic layer is dried over MgSO$_4$, filtrated and concentrated. The residue is purified by flash chromatography (cyclohexane/ethyl acetate=8/2) and concentrated. Yield 97% m/z 291/335/391 [M+H]+, rt 1.36 min, LC-MS Method V012_S01.

And for the synthesis of I-1.2.1 an aq. solution of sodium carbonate (2 mol/L) is used instead of the potassium phosphate solution.

Step 3: Synthesis of Intermediate I-1.3

I-1.2 (4.85 g, 10.9 mmol) is dissolved in formic acid. The mixture is heated to 50 OC for 25 min in a pressure vessel. The reaction mixture is dropped carefully in saturated NaHCO$_3$ solution and then extracted three times with ethyl acetate. The organic layer is dried over MgSO$_4$, filtrated and then concentrated. The residue is purified by flash chromatography (DCM/methanol=98/2). Yield 28%. m/z 344/361 [M+H]+/[M+NH4]+, rt 0.85 min, LC-MS Method V011_S01.

The following intermediates as shown in Table 4 are synthesized in a similar fashion from the appropriate intermediate:

TABLE 4

| Intermediate | Educt | Structure of Intermediate | m/z [M + H]+ | rt (min) | LC-MS method |
|---|---|---|---|---|---|
| I-1.3.1 | I-1.2.1 | | 396 | 0.96 | V012_S01 |
| I-1.3.2 | I-1.2.2 | | 292 | n.d. | n.d. |
| I-1.3.3 | I-1.2.3 | | 344 | 0.76 | V018_S01 |

TABLE 4-continued

| Intermediate | Educt | Structure of Intermediate | m/z [M + H]+ | rt (min) | LC-MS method |
|---|---|---|---|---|---|
| I-1.3.4 | I-1.2.4 | (structure) | 346 | 0.96 | V011_S01 |

During the synthesis of intermediates I-1.3.1, I-1.3.2, I-1.3.3 and I-1.3.4 p-toluenesulfonic acid monohydrated in acetonitrile is added to the educt and the reaction mixture is stirred for 12 h.

Step 4: Synthesis of Intermediate I-1.4

To R4 (50 mg, 0.20 mmol) in DMF (1.5 mL) HATU (82 mg, 0.22 mmol) and diisopropylethylamine (135 µL, 0.78 mmol) are added and the reaction mixture is stirred for 15 min. Then intermediate I-1.3 (71 mg, 0.21 mmol) is added and the mixture is stirred for additional 12 h. The reaction solution is directly purified by reversed phase HPLC. Yield 75%, m/z 581/525/481 [M+H]+, rt 1.17 min, LC-MS Method V011_S01.

The following intermediates as shown in Table 5 are synthesized in a similar fashion from the appropriate intermediate:

TABLE 5

| Intermediate | Educt | Structure of Intermediate | m/z [M + H]+ | rt (min) | LC-MS method |
|---|---|---|---|---|---|
| I-1.4.1 | I-1.3.1 | (structure) | 433/477/533 | 1.32 | V011_S01 |
| I-1.4.2 | I-1.3.2 | (structure) | 529 | 1.46 | V002_005 |

TABLE 5-continued

| Intermediate | Educt | Structure of Intermediate | m/z [M + H]+ | rt (min) | LC-MS method |
|---|---|---|---|---|---|
| I-1.4.3 | I-1.3.3 | 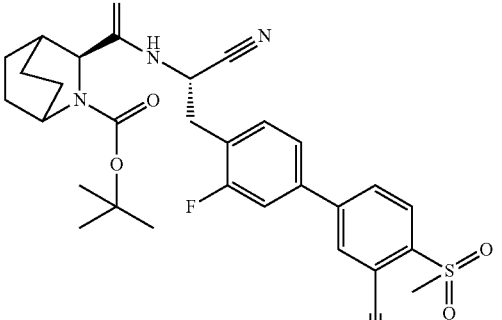 | 581 | 1.25 | V018_S01 |
| I-1.4.4 | I-1.3.4 | 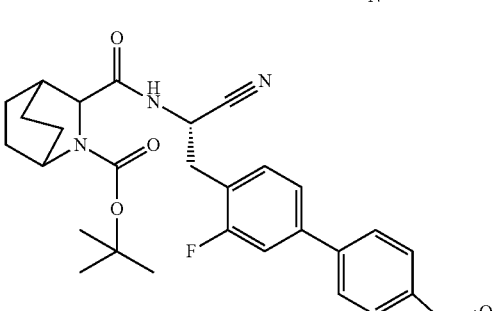 | 583 | 1.27 | V011_S01 |

During the synthesis of intermediates I-1.4.2 TBTU is used instead of HATU.

Step 5: Synthesis of Example 1

I-1.4 (85 mg, 0.15 mmol) is dissolved in formic acid. The mixture is heated to 50° C. for 15 min in a pressure vessel. The product is purified by reversed phase HPLC. Yield 79%, m/z 481 [M+H]+, rt 1.08 min, LC-MS Method V011_S01.

Method B

Synthesis of (2S)—N-[(1S)-1-cyano-2-[4-(2-oxoindolin-6-yl)phenyl]ethyl]-3-azabicyclo[2.2.2]octane-2-carboxamide (Example 2)

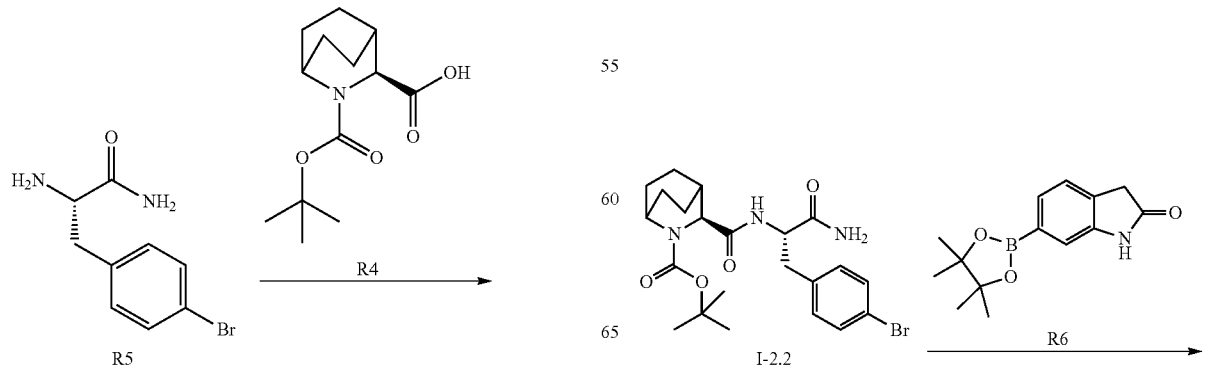

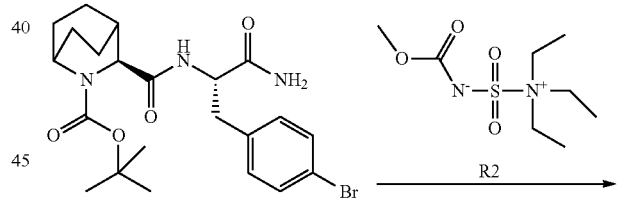

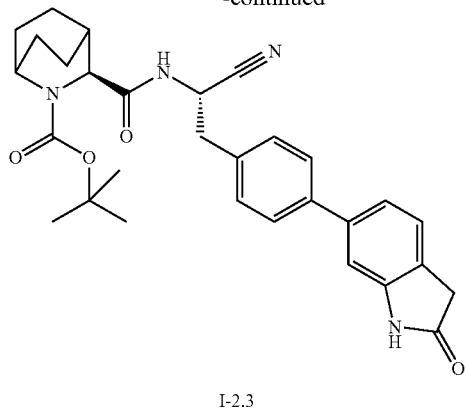

I-2.3

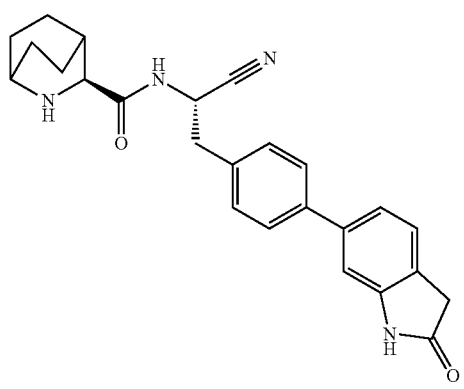

Example 2

Step 1: Synthesis of Intermediate I-2.1

R4 (1.62 g, 6.16 mmol) is dissolved in DCM (60 mL) and the mixture is purged with argon. Then 1.5 equivalents diisopropylethylamine (1.45 mL, 8.40 mmol) and HATU (2.34 g, 6.16 mmol) are added and the mixture is stirred for 30 min. R5 (2.00 g, 5.60 mmol) and additional 1.5 equivalent diisopropylethylamine (1.45 mL, 8.40 mmol) are added and the reaction mixture is stirred for 12 h. To the resulting mixture water is added and the DCM phase is extracted 3 times with water. The organic layer is washed with brine and concentrated. The crude product is purified by HPLC. Yield 67%, m/z 480 [M+H]+, rt 0.95 min, LC-MS Method Z018_S04.

Step 2: Synthesis of Intermediate I-2.2

I-2.1 (1.95 g, 4.06 mmol) is stirred in anhydrous DCM (30 mL) under argon for 15 min. Afterwards R2 (1.94 g, 8.13 mmol) is added and the reaction mixture is stirred for 12 h under argon. Because educt I-2.1 is still remaining, additional 1.5 eq educt R2 are added and the solution is stirred for additional 3 h. DCM and 2 M $Na_2CO_3$ solution are added to the reaction mixture. The organic layer is extracted two times with $Na_2CO_3$ solution (2 mol/L) and two times with tartaric acid (10%). The combined organic layers are dried over $MgSO_4$ and concentrated. The product is dissolved in water/acetonitrile and freeze-dried. Yield 97% m/z 462/406/362 [M+H]+, rt 1.04 min, LC-MS Method Z018_S04.

Step 3: Synthesis of Intermediate I-2.3

R6 (34 mg, 0.13 mmol) and I-2.2 (46 mg, 0.10 mmol) are put together in vented acetonitrile (3 mL) and then aq. potassium carbonate solution (2 mol/L, 100 μL) is added. Then 1,1-Bis(di-tert-butylphosphino)ferrocene palladium dichloride (7 mg, 0.01 mmol) is added quickly and the reaction vessel is purged with argon. The reaction mixture is heated to 80° C. for 2 h. Further 0.5 eq of educt R6 and further 0.1 eq of the catalyst are added and the reaction mixture is stirred at 80° C. for additional 12 h. The resulting mixture is filtrated over a mixture of basic aluminium oxide and silica gel 1/1. The residue is purified by reversed phase HPLC. Yield 41% m/z 514 [M+H]+, rt 0.92 min, LC-MS Method Z018_S04.

The following intermediates as shown in Table 6 are synthesized in a similar fashion from the appropriate intermediate:

TABLE 6

| Intermediate | Structure | m/z [M + H]+ | rt (min) | LC-MS method |
|---|---|---|---|---|
| I-2.3.1 | 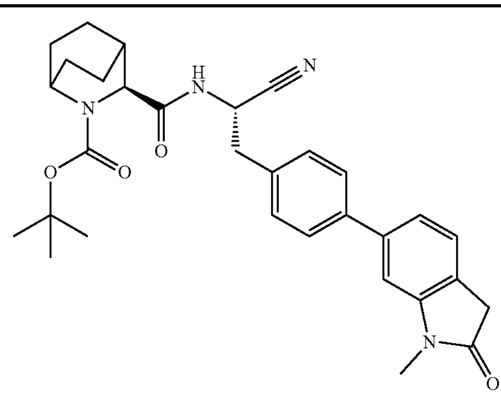 | 429 (M − BOC) + H+ | 0.92 | Z011_S03 |

TABLE 6-continued

| Intermediate | Structure | m/z [M + H]+ | rt (min) | LC-MS method |
| --- | --- | --- | --- | --- |
| I-2.3.2 | 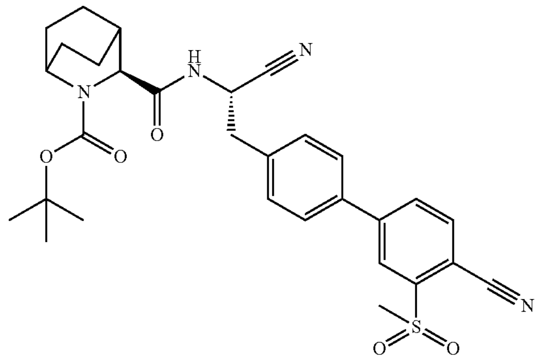 [SMILES: CC(C)(C)OC(=O)N1C2CCC(CC2)[C@H]1C(=O)N[C@H](C#N)Cc1ccc(-c2ccc(C#N)c(S(C)(=O)=O)c2)cc1] | 563 | 0.91 | Z011_S03 |
| I-2.3.3 | 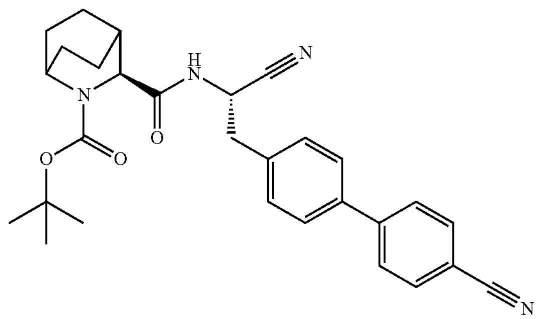 [SMILES: CC(C)(C)OC(=O)N1C2CCC(CC2)[C@H]1C(=O)N[C@H](C#N)Cc1ccc(-c2ccc(C#N)cc2)cc1] | 485 | 1.24 | 001_CA04 |
| I-2.3.4 | 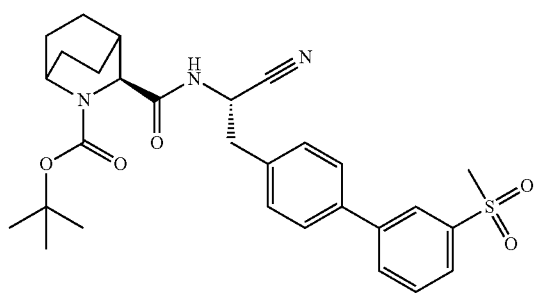 [SMILES: CC(C)(C)OC(=O)N1C2CCC(CC2)[C@H]1C(=O)N[C@H](C#N)Cc1ccc(-c2cccc(S(C)(=O)=O)c2)cc1] | 538 | 0.82 | Z018_S04 |
| I-2.3.5 | 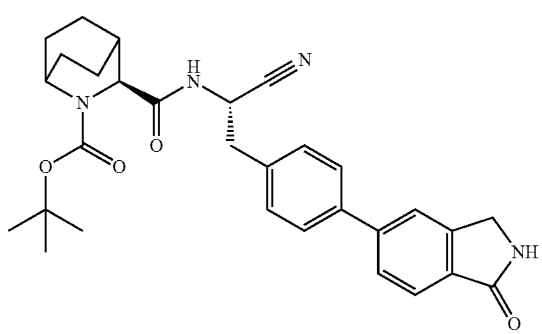 [SMILES: CC(C)(C)OC(=O)N1C2CCC(CC2)[C@H]1C(=O)N[C@H](C#N)Cc1ccc(-c2ccc3c(c2)CNC3=O)cc1] | 515 | 0.88 | Z018_S04 |

TABLE 6-continued
| Intermediate | Structure | m/z [M + H]+ | rt (min) | LC-MS method |
| --- | --- | --- | --- | --- |
| I-2.3.6 | 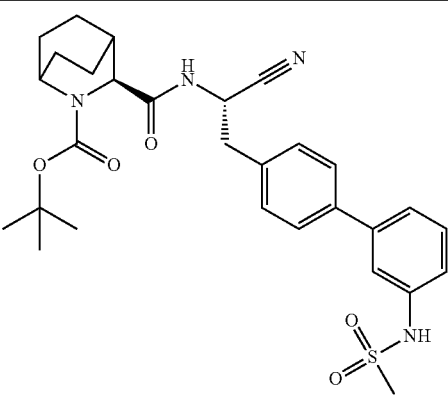 | 553 | 1.06 | 001_CA04 |
| I-2.3.7 | 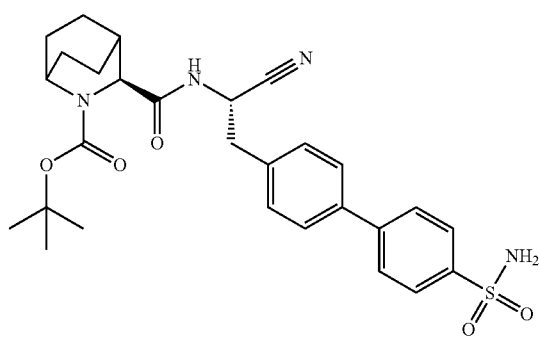 [SMILES: CC(C)(C)OC(=O)N1C2CCC(CC2)[C@H]1C(=O)N[C@H](C#N)Cc1ccc(-c2ccc(S(N)(=O)=O)cc2)cc1] | 539 | 1.08 | 001_CA04 |
| I-2.3.8 | 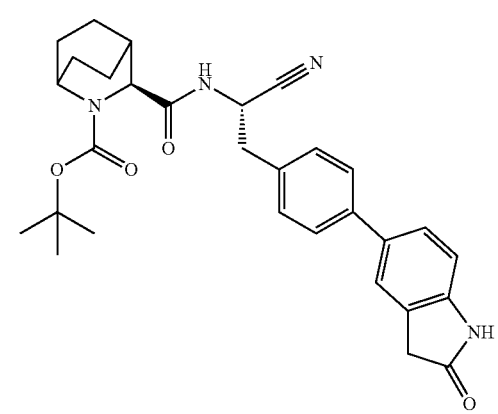 [SMILES: CC(C)(C)OC(=O)N1C2CCC(CC2)[C@H]1C(=O)N[C@H](C#N)Cc1ccc(-c2ccc3c(c2)CC(=O)N3)cc1] | 515 | 0.91 | Z018_S04 |
| I-2.3.9 | 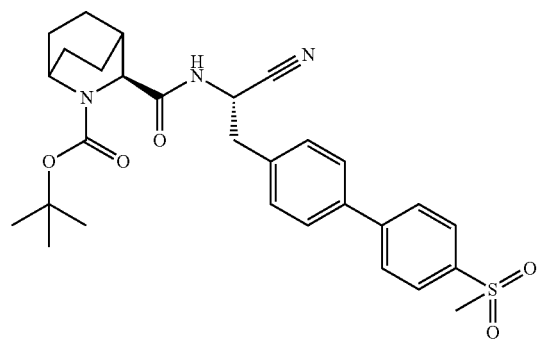 [SMILES: CC(C)(C)OC(=O)N1C2CCC(CC2)[C@H]1C(=O)N[C@H](C#N)Cc1ccc(-c2ccc(S(C)(=O)=O)cc2)cc1] | 538 | 0.83 | Z018_S04 |

TABLE 6-continued
| Intermediate | Structure | m/z [M + H]+ | rt (min) | LC-MS method |
| --- | --- | --- | --- | --- |
| I-2.3.10 | 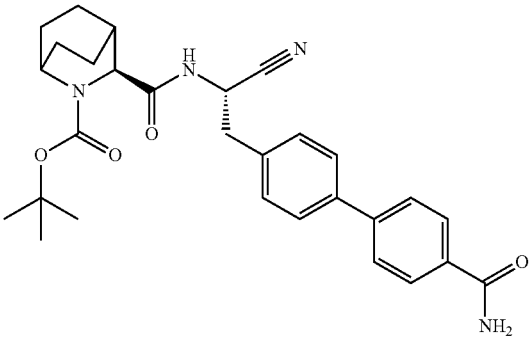 [SMILES: CC(C)(C)OC(=O)N1C2CCC(CC2)[C@H]1C(=O)N[C@H](C#N)Cc1ccc(-c2ccc(C(N)=O)cc2)cc1] | 503 | 0.84 | Z011_S03 |
| I-2.3.11 | 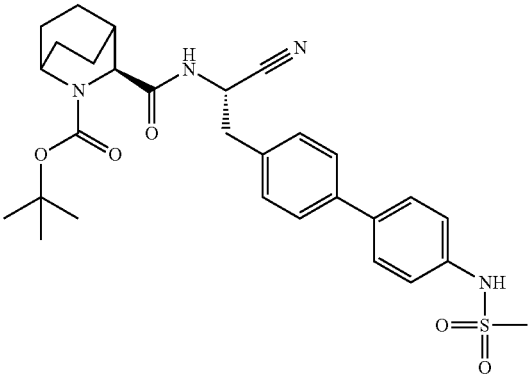 [SMILES: CC(C)(C)OC(=O)N1C2CCC(CC2)[C@H]1C(=O)N[C@H](C#N)Cc1ccc(-c2ccc(NS(C)(=O)=O)cc2)cc1] | 553 | 1.01 | 001_CA04 |
| I-2.3.12 | 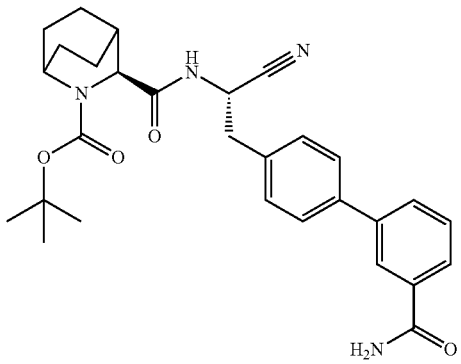 [SMILES: CC(C)(C)OC(=O)N1C2CCC(CC2)[C@H]1C(=O)N[C@H](C#N)Cc1ccc(-c2cccc(C(N)=O)c2)cc1] | 503 | 1.01 | 001_CA04 |
| I-2.3.13 | 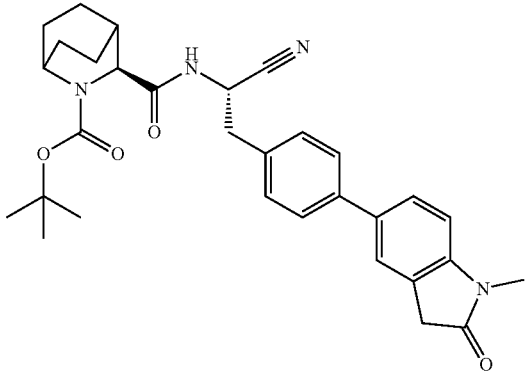 [SMILES: CN1C(=O)Cc2cc(-c3ccc(C[C@@H](C#N)NC(=O)[C@@H]4C5CCC(CC5)N4C(=O)OC(C)(C)C)cc3)ccc21] | 529 | 0.97 | Z018_S04 |

TABLE 6-continued
| Intermediate | Structure | m/z [M + H]+ | rt (min) | LC-MS method |
| --- | --- | --- | --- | --- |
| I-2.3.14 | 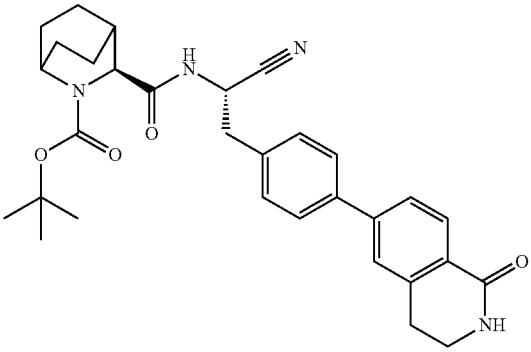 [SMILES: CC(C)(C)OC(=O)N1C2CCC(CC2)[C@H]1C(=O)N[C@H](C#N)Cc1ccc(-c2ccc3c(c2)CCNC3=O)cc1] | 529 | 1.07 | 001_CA04 |
| I-2.3.15 | 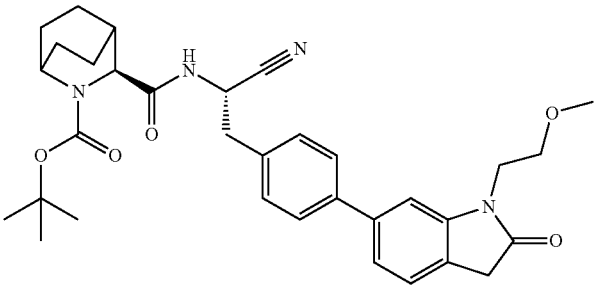 [SMILES: COCCN1C(=O)Cc2ccc(-c3ccc(C[C@@H](C#N)NC(=O)[C@@H]4C5CCC(CC5)N4C(=O)OC(C)(C)C)cc3)cc21] | 573 | 0.76 | Z018_S04 |
| I-2.3.16 | 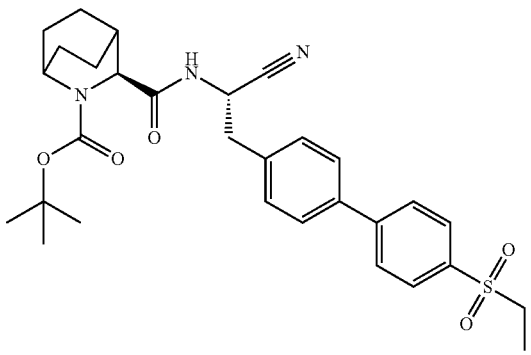 [SMILES: CCS(=O)(=O)c1ccc(-c2ccc(C[C@@H](C#N)NC(=O)[C@@H]3C4CCC(CC4)N3C(=O)OC(C)(C)C)cc2)cc1] | 552 | 1.20 | 001_CA04 |
| I-2.3.17 | 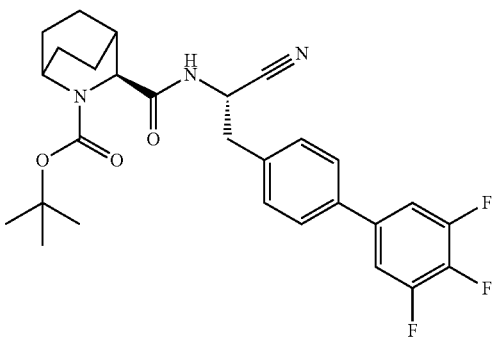 [SMILES: CC(C)(C)OC(=O)N1C2CCC(CC2)[C@H]1C(=O)N[C@H](C#N)Cc1ccc(-c2cc(F)c(F)c(F)c2)cc1] | 514 | 1.43 | 001_CA04 |

TABLE 6-continued

| Intermediate | Structure | m/z [M + H]+ | rt (min) | LC-MS method |
|---|---|---|---|---|
| I-2.3.18 | 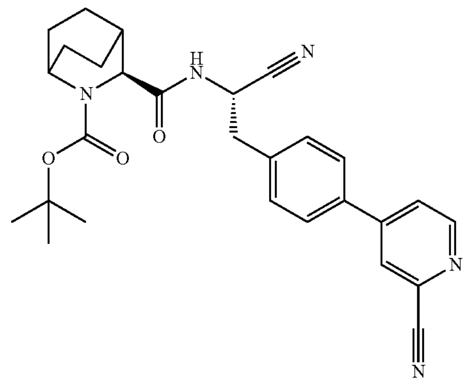 [SMILES: CC(C)(C)OC(=O)N1C2CCC(CC2)[C@H]1C(=O)N[C@H](C#N)Cc1ccc(-c2ccnc(C#N)c2)cc1] | 486 | 1.19 | 001_CA04 |

Step 4: Synthesis of Example 2

To I-2.3 (31 mg, 0.06 mmol) in acetonitrile (1 mL) p-toluenesulfonic acid monohydrate (34 mg, 0.18 mmol) is added and the mixture is stirred for 12 h. The reaction mixture is diluted with DMF and directly purified by reversed phase HPLC. Yield 45%, m/z 415 [M+H]+, rt 0.66 min, LC-MS Method Z018_S04.

Method C

Synthesis of (2S)—N-[(1S)-1-cyano-2-[4-(4-cyano-3-fluoro-phenyl)phenyl]ethyl]-3-azabicyclo[2.2.2]octane-2-carboxamide (Example 7)

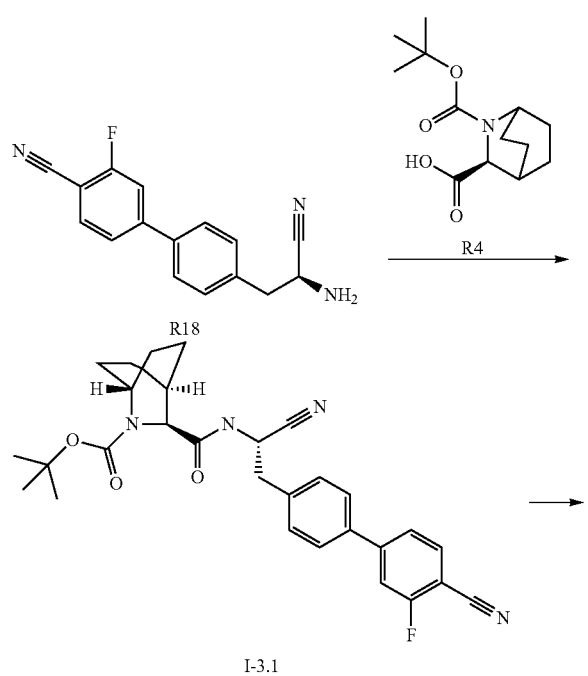

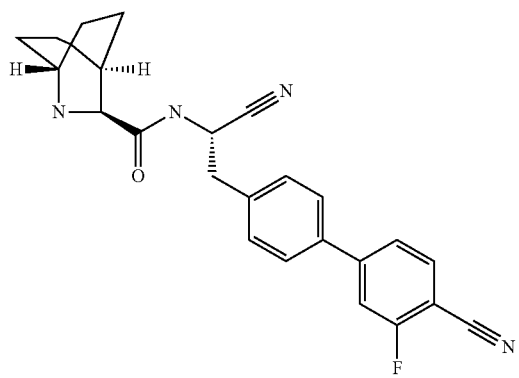

Example 7

Step 1: Synthesis of Intermediate I-3.1

To R4 (200 mg, 0.78 mmol) in DMF (5 mL) is added TBTU (290.48 mg, 0.91 mmol) and DIPEA (0.26 mL, 1.51 mmol). R18 (200 mg, 0.75 mmol) is added and stirred for 3 h at r.t. Potassium carbonate is added and the reaction mixture is filtered over basic alox. The residue is purified over silica gel (cyclohexane/ethyl acetate 100:0-50:50) to give the intermediate I-3.1. Yield 45%.

Step 2: Synthesis of Example 7

I-3.1 (170 mg, 0.34 mmol) and formic acid (1 mL) is stirred 2 h at r.t. The reaction mixture is diluted with methanol and purified by reversed phase HPLC.

Yield 23% m/z 403 [M+H]+, rt 1.15 min, LC-MS Method V002_005.

Synthesis of Starting Materials/Educts

Amino Acids

Synthesis of tert-butyl N-[(1S)-2-amino-1-[(4-bromo-2-fluoro-phenyl)methyl]-2-oxo-ethyl]carbamate (R1)

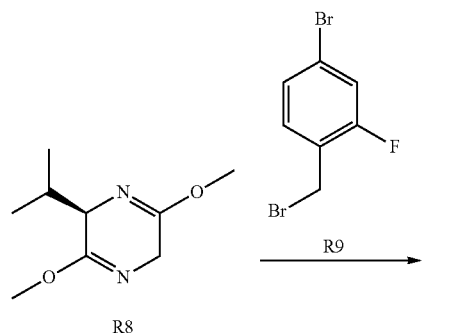

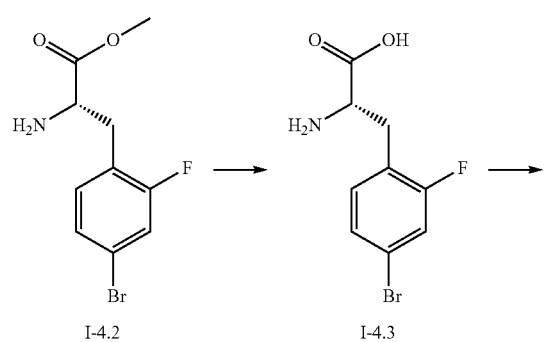

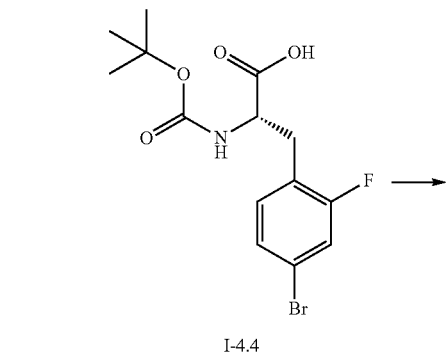

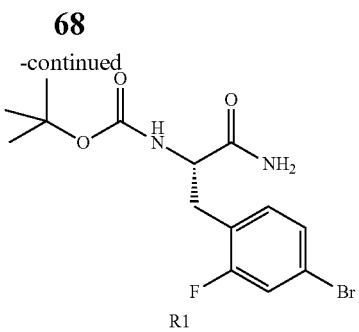

Step 1: Synthesis of Intermediate I-4.1

R8 (212 g, 1151 mmol) in tetrahydrofuran (dry) (600 mL) is cooled to −78° C. Then n-butyllithium (2.5 M in hexanes, 552 mL, 1381 mmol) is added dropwise, keeping the temperature below −78° C. After 30 min R9 (324 g, 1209 mmol) in tertahydrofuran (dry) (120 mL) is added dropwise. The reaction mixture is stirred at −78° C. for 1 h. The mixture is quenched with saturated NH$_4$Cl solution and extracted three times with ethyl acetate. The organic layer is washed with brine, dried over Na$_2$SO$_4$ and evaporated in vacuo. The residue is purified by flash chromatography (heptane/ethyl acetate=80/20). Yield 60%.

Step 2: Synthesis of Intermediate I-4.2

To I-11.1 (104 g, 265 mmol) in acetonitrile (600 mL) aq. 0.2 M HCl (2788 mL, 558 mmol) is added.

The mixture is stirred at RT for 12 h. The mixture is extracted with diethylether and the pH of the aq. layer is adjusted to ~8 with sat. NaHCO$_3$-solution. Then it is extracted three times with ethyl acetate. The organic layer is washed with brine, dried over Na$_2$SO$_4$ and concentrated. Yield 80%.

Step 3: Synthesis of Intermediate I-4.3

I-11.2 (62.4 g, 211 mmol) is stirred in aq. 3 M HCl (3 mol/L, 1000 mL) at 60° C. for 16 h. The mixture is cooled down and the pH is adjusted to ~7 with aq. 6 M NaOH. Then the reaction mixture is filtered, washed three times with water and dried in a vacuum oven at 40° C. for 12 h. Yield 74%.

Step 4: Synthesis of Intermediate I-4.4

To I-11.3 (151 g, 546 mmol) in 1,4-dioxane (2.2 L) is added aq. 2 M sodium carbonate (301 mL) and di-tertbutyl dicarbonate (138 g, 147 mL). The mixture is stirred for 4 h. Then water is added and the pH is adjusted to ~4-5 with citric acid. The mixture is extracted three times with ethyl acetate. The organic layer is washed with brine, dried over Na$_2$SO$_4$ and concentrated. The residue is stirred in heptane for 15 min and the product is filtered off. Yield 87%.

The following intermediate as shown in Table 8.1 is synthesized in a similar fashion from the appropriate intermediate:

TABLE 8.1

| Intermediate | Structure | m/z [M + H]+ | rt (min) | LC-MS method |
|---|---|---|---|---|
| I-4.4.1 | 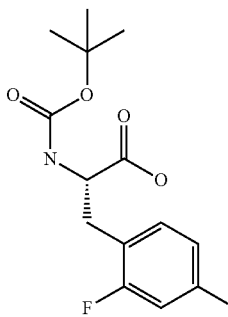 | 410 | 1.21 | V012_S01 |

Step 5: Synthesis of R1

To I-11.4 (181 g, 476 mmol) in dry DMF (1200 mL) N-methylmorpholine (72 g, 713 mmol) and TBTU (153 g, 476 mmol) are added and the reaction mixture is stirred for 30 min. Then the reaction mixture is cooled to 0° C. and aq. 35% ammonium solution (47 mL, 856 mmol) is added and the mixture is stirred at room temperature for 12 h. Water is added and the formed product is filtered off and washed three times with water. The product is dried in a vacuum oven at 40° C. for 72 h. Yield 64%.

The following intermediates as shown in Table 8.2 are synthesized in a similar fashion from the appropriate intermediate:

TABLE 8.2

| Intermediate | Structure | m/z [M + H]+ | rt (min) | LC-MS method |
|---|---|---|---|---|
| R1.1 | 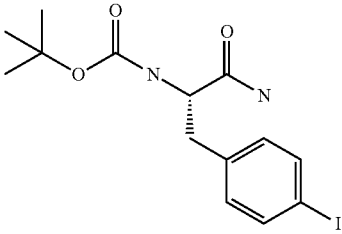 | 391 | 1.10 | V011_S01 |
| R1.2 | 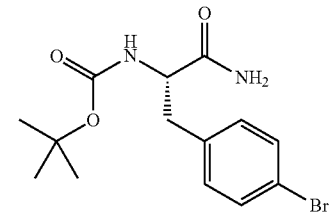 | 343 | 1.39 | Z002_005 |
| R1.3 | 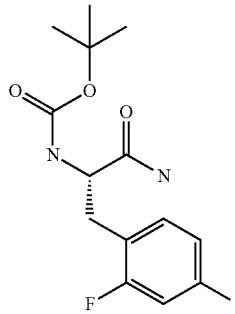 | 409 | 1.05 | V011_S01 |

Synthesis of 4-[4-[(2S)-2-amino-2-cyano-ethyl]phenyl]-2-fluoro-benzonitrile (R18)

Synthesis of (2S)-2-amino-3-(4-bromophenyl)propanamide (R5)

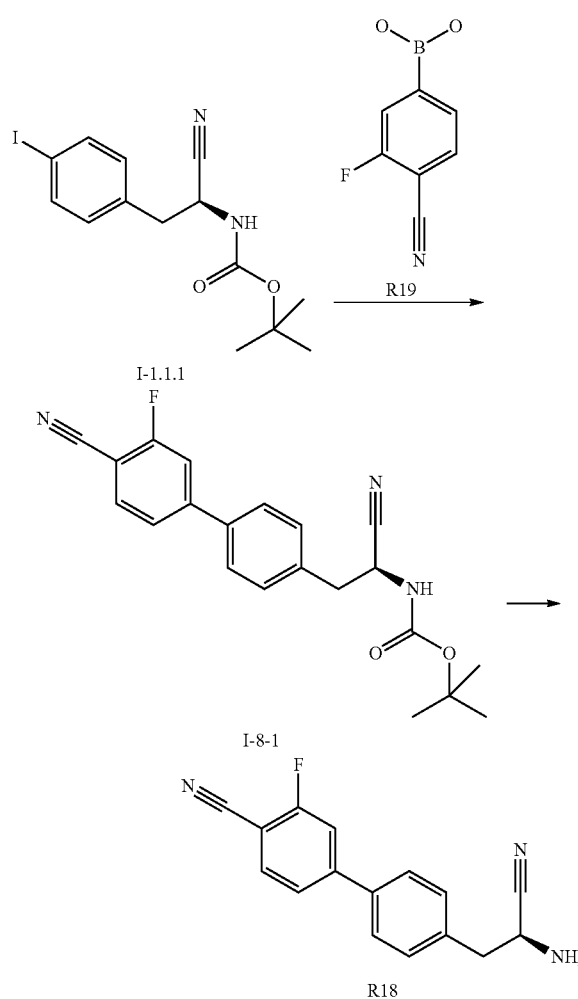

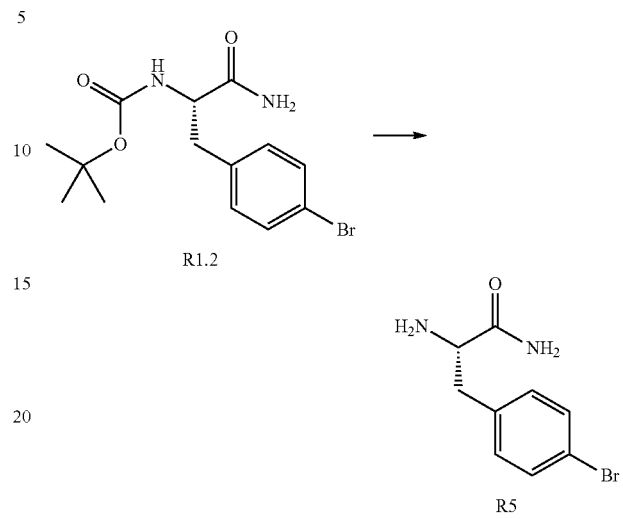

To R1.2 (2.00 g, 5.8 mmol) in DCM (12 mL) TFA (4 mL) is added and the reaction mixture is stirred for 3 h. Then the reaction mixture is concentrated, the residue is dissolved in DCM and water. The solution is freeze-dried. Yield >95% m/z 243 [M+H]+, rt 0.52 min, LC-MS Method Z018_S04.

Amines

Synthesis of (2S)-3-tert-butoxycarbonyl-3-azabicyclo[2.2.2]octane-2-carboxylic acid (R4)

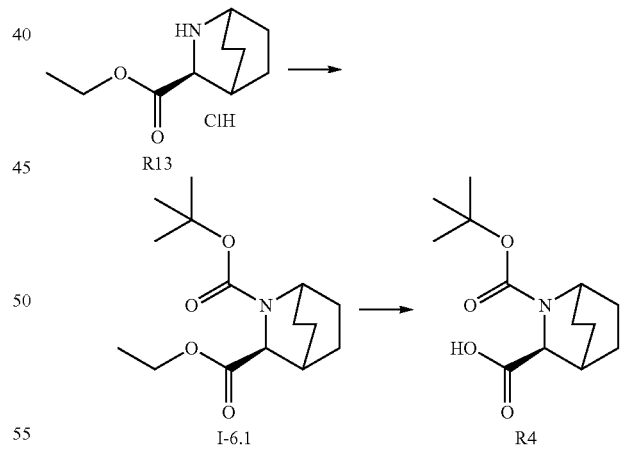

Step 1: Synthesis of Intermediate I-8.1

To 4-cyano-3-fluoroboronic acid (0.16 g, 0.97 mmol) in dioxane (10 mL) is added I-1.1.1 (0.3 g, 0.81 mmol) and Bis(bis(1,2-diphenylphosphino)ethane)palladium(O) (10 mg, 0.01 mmol) and degassed with nitrogen for 15 min. A solution of potassium carbonate (0.23 g, 1.63 mmol) in water (1 mL) is added and again degassed for 15 min. The reaction mixture is stirred at 80° C. overnight and afterwards concentrated in vacuo. The crude residue is diluted with ethyl acetate and extracted with water and brine, dried over sodium sulfate and concentrated. The crude product is purified over column chromatography (ethyl acetate/hexane 1:4). Yield: 54%.

Step 2: Synthesis of R18

I-8.1 (0.16 g, 0.44 mmol) is dissolved in formic acid (2 mL) and stirred at 50° C. for 20 min. The reaction mixture is concentrated in vacuo and the residue is purified over column chromatography (dichloromethane/methanol 98:2). Yield: 52%.

Step 1: Synthesis of Intermediate I-6.1

To R13 (1.00 g, 4.6 mmol) in THF (20 mL) are added 1 M NaOH (10 mL, 10.0 mmol) and di-tert-butyldicarbonat (1.19 g, 5.5 mmol) and the reaction mixture is stirred at 70° C. for 12 h. The pH is adjusted to 4 with 1 M HCl. The mixture is extracted with DCM. The organic layer is dried over MgSO4 and concentrated. Yield >95%, m/z 284 [M+H]+, rt 0.78 min, LC-MS Method X001_004.

Step 2: Synthesis of R4

To I-6.1 (3.50 g, 12.4 mmol) in dioxane (30 mL) is added LiOH (0.44 g, 18.5 mmol)—dissolved in 6 mL water—dropwise. The reaction mixture is heated to 60° C. for 12 h. Additional 3.5 eq LiOH are added and the mixture is heated to 60° C. for additional 24 h. The reaction mixture is extracted with water and DCM. The aq. layer is acidified with HCl and extracted three times with DCM. The organic layer is dried over MgSO$_4$ and concentrated. Yield >95%, m/z 256 [M+H]+, rt 0.82 min, LC-MS Method Z018_S04.

Halogenides

Synthesis of 5-bromo-2-methyl-isoindoline (R15)

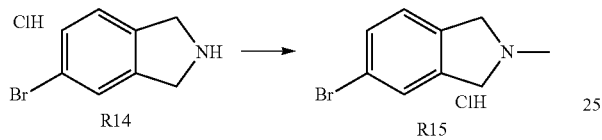

The pH of a mixture of R14 (1.85 g, 7.9 mmol) in methanol (100 mL) and water (10 mL) is adjusted to ~5 with acetic acid. Then a 37% formalin solution (1.28 mL, 15.8 mmol) is added and the mixture is stirred for 15 min. Sodium cyanoborohydride (0.74 g, 11.8 mmol) is added and the reaction mixture is stirred for additional 12 h. The mixture is concentrated and ethyl acetate and aq. 1 M NaOH solution is added to the residue. The organic layer is washed with NaCl solution, dried over MgSO$_4$ and concentrated. The residue is dissolved in diethyl ether and ethereal HCl is added dropwise. The resulting precipitation is filtered off. Yield 62% m/z 212/214 [M+H]+, rt 0.65 min, LC-MS Method V012_S01.

Synthesis of 5-bromo-2-methylsulfonyl-benzonitrile (R17)

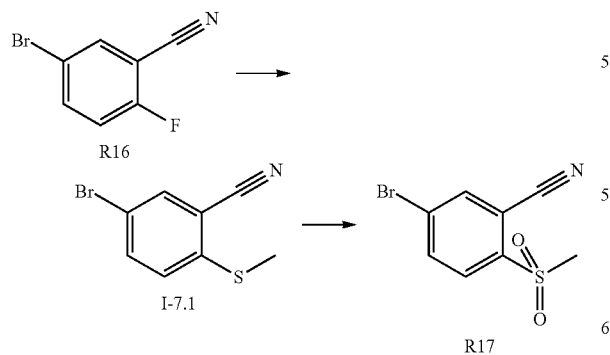

Step 1: Synthesis of Intermediate I-7.1

To 5-Bromo-2-fluoro-benzonitrile (10.05 g, 50.25 mmol) in DMSO (30 mL) is added sodiummethanethiolate (3.87 g, 55.27 mmol) portionwise at 0° C. The reaction mixture is stirred for 2 h at r.t. Sodiummethanethiolate (1.06 g, 15.07 mmol) is added and stirred for further 2 h at r.t. The reaction mixture is diluted with water (100 mL) and the precipitate is filtered off and dried in vacuo at 50° C.

Yield 88% m/z 228/230 [M+H]+, rt 1.26 min, LC-MS Method V018_S01.

Step 2: Synthesis of R17

To I-7.1 (10.10 g, 44.28 mmol) in dichloromethane is added 3-chloroperoxybenzoic acid (19.85 g, 88.55 mmol) at 0° C. and stirred overnight at r.t. 3-chloroperoxybenzoic acid (3.97 g, 17.71 mmol) is added and stirred again overnight at r.t. The precipitate is filtered off and the filtrate is extracted with saturated sodium hydrogencarbonate solution. The aq. layer is washed with dichloromethane. The organic layers are combined, dried over MgSO$_4$ and concentrated.

Yield 97% m/z 277/279 [M+H]+, rt 0.88 min, LC-MS Method V011_S01.

Boronic Acids or Esters

Synthesis of 1-Methyl-6-(4,4,5,5-tetramethyl-[1,3,2]dioxaborolan-2-yl)-1,3-dihydro-indol-2-one (R12

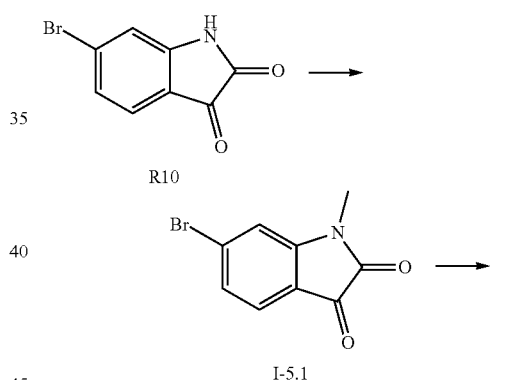

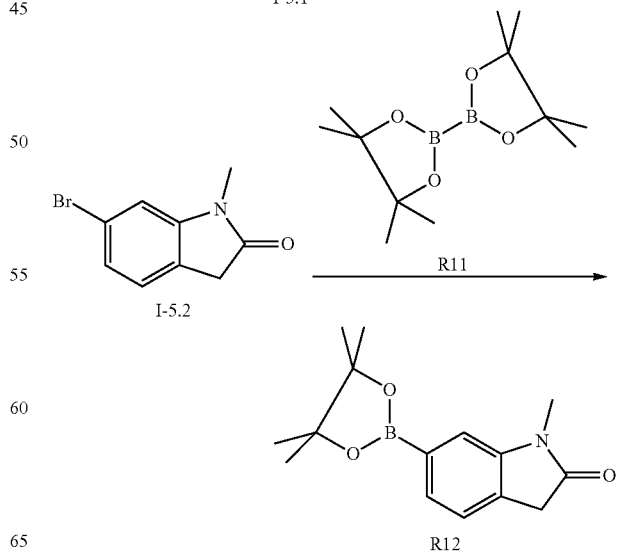

Step 1: Synthesis of Intermediate I-5.1

To R10 (25.0 g, 111 mmol) in acetonitrile (750 mL) is added MeI (15 mL, 241 mmol) and $K_2CO_3$ (60.0 g, 434 mmol) and the reaction mixture is stirred at 60° C. for 2 h. The reaction mixture is filtered and concentrated. Water and ethyl acetate are added to the residue. The organic layer is extracted twice with water, is dried over $MgSO_4$ and concentrated. Yield 56%, m/z 240/242 [M+H]+, rt 0.48 min, LC-MS Method X001_004.

The following intermediates as shown in Table 9 are synthesized in a similar fashion from the appropriate intermediate:

TABLE 9

| Intermediate | Structure | m/z [M + H]+ | rt (min) | LC-MS method |
|---|---|---|---|---|
| I-5.1.1 | (structure) | 284/286 | 1.12 | V003_003 |
| I-5.1.2 | (structure) | 240/242 | 0.49 | X001_004 |

Step 2: Synthesis of Intermediate I-5.2

I-5.1 (15.0 g, 63 mmol) and hydrazine hydrate (30 mL, 618 mmol) are heated to 125° C. for 72 h. To the cool reaction mixture DCM is added and extracted with water and 1 M HCl. The organic layer is dried over $MgSO_4$ and concentrated. The crystallized residue is dissolved in DCM, methanol is added and the DCM is removed under vacuum. The crystallized product is filtered with sunction and washed with cold methanol. Yield 63%, m/z 226/228 [M+H]+, rt 1.16 min, LC-MS Method V001_003.

The following intermediate as shown in Table 10 is synthesized in a similar fashion from the appropriate intermediate:

TABLE 10

| Intermediate | Structure | m/z [M + H]+ | rt (min) | LC-MS method |
|---|---|---|---|---|
| I-5.2.1 | (structure) | 270 | 0.83 | Z018_S04 |
| I-5.2.2 | (structure) | 226 | 0.80 | Z018_S04 |

Step 3: Synthesis of Intermediate R12

To I-5.2 (32.0 g, 142 mmol) in anhydrous dioxane (400 mL) is added R11 (54.4 g, 241 mmol) and potassium acetate (41.6 g, 424 mmol). The mixture is purged with Argon, [1,1'-Bis(diphenylphosphino)ferrocene]dichloropalladium(II) as a complex with dichloromethane (11.2 g, 14 mmol) is added and the mixture is heated to 90° C. for 2 h. The reaction mixture is diluted with ethyl acetate and water, the organic layer is washed with water, dried over $MgSO_4$ and concentrated. The residue is purified via flash chromatography (cyclohexane/EA=70:30). Yield 72%, m/z 274 [M+H]+, rt 0.67 min, LC-MS Method V011_S01.

The following intermediates as shown in Table 1 are synthesized in a similar fashion from the appropriate intermediate:

TABLE 11

| Intermediate | Structure | m/z [M + H]+ | rt (min) | LC-MS method |
|---|---|---|---|---|
| R3 | 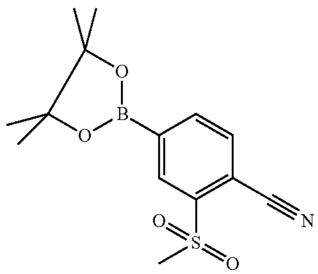 | 325 [M + NH$_4$]+ | 0.30 | X018_S01 |
| R12.1 | 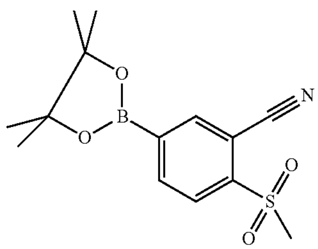 | 226 (boronic acid) | 0.66 | V018_S01 |
| R12.2 | 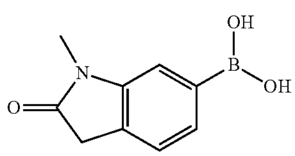 | 192 | 0.91 | Z018_S04 |
| R12.3 | 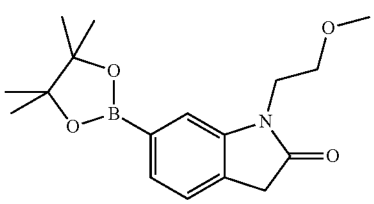 | 318 | 0.55 | Z018_S04 |
| R12.4 | 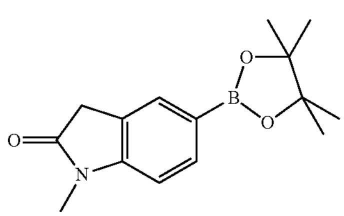 | 274 | 0.91 | Z018_S04 |

EXAMPLES (rt=retention time) Deprotection Methods: TSA (toluene sulfonic acid cf. Example 2), SI (trimethylsilyl iodide cf. example 3), FA (formic acid cf. example 1), TFA (trifluoroacetic acid).

TABLE 12

| Example | Structure | Educt | Syn./Deprot. Method | Yield [%] |
|---|---|---|---|---|
| 1 | 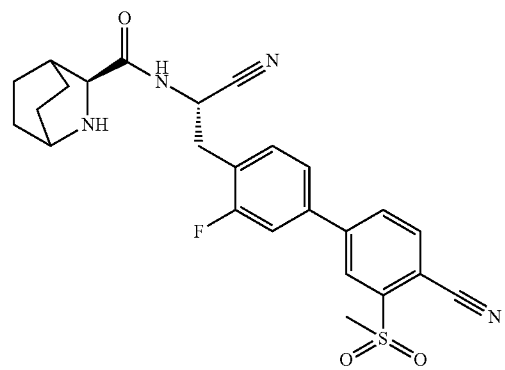 [SMILES: CS(=O)(=O)c1cc(-c2ccc(C[C@@H](C#N)NC(=O)[C@H]3NC4CCC3CC4)c(F)c2)ccc1C#N] | I-1.4 | A/FA | 79 |
| 2 | 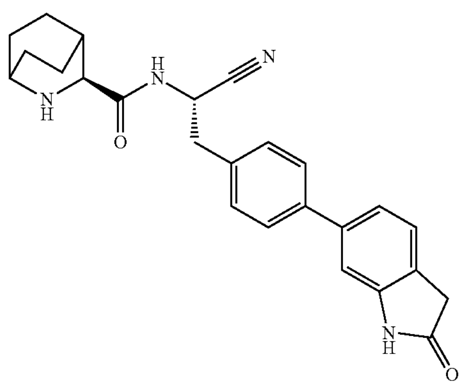 [SMILES: N#C[C@H](Cc1ccc(-c2ccc3c(c2)NC(=O)C3)cc1)NC(=O)[C@H]1NC2CCC1CC2] | I-2.3 | B/TSA | 45 |
| 4 | 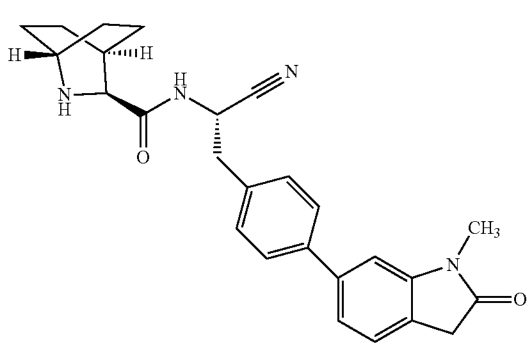 [SMILES: CN1C(=O)Cc2ccc(-c3ccc(C[C@@H](C#N)NC(=O)[C@H]4N[C@H]5CC[C@@H]4CC5)cc3)cc21] | I-1.4.2 | A/FA | 33 |

TABLE 12-continued
| Example | Structure | Educt | Syn./Deprot. Method | Yield [%] |
|---|---|---|---|---|
| 6 | 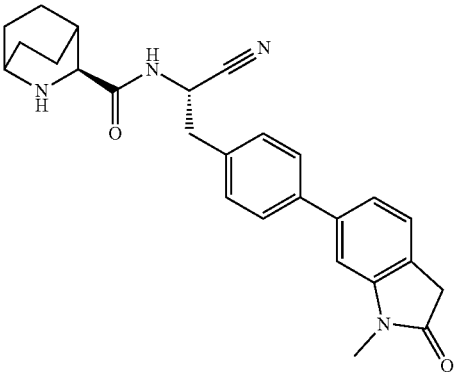 [SMILES: CN1C(=O)Cc2ccc(-c3ccc(C[C@@H](C#N)NC(=O)[C@H]4NC5CCC4CC5)cc3)cc21] | I-2.3.1 | B/TSA | 53 |
| 7 | 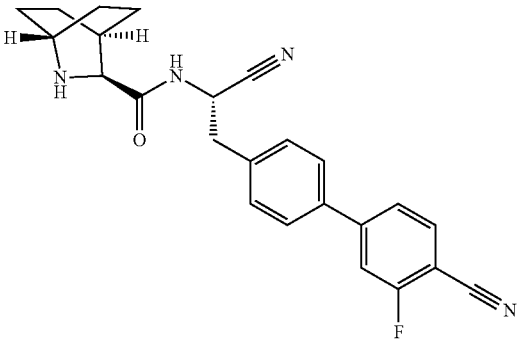 [SMILES: N#Cc1ccc(-c2ccc(C[C@@H](C#N)NC(=O)[C@H]3N[C@H]4CC[C@@H]3CC4)cc2)cc1F] | I-3.1. | C/FA | 23 |
| 8 | 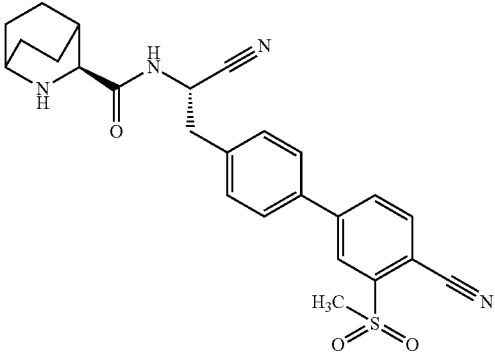 [SMILES: CS(=O)(=O)c1cc(-c2ccc(C[C@@H](C#N)NC(=O)[C@H]3NC4CCC3CC4)cc2)ccc1C#N] | I-2.3.2 | B/TSA | 83 |
| 9 | 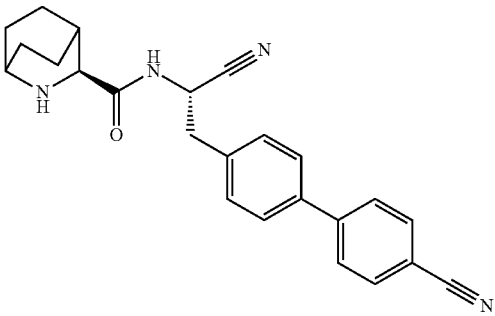 [SMILES: N#Cc1ccc(-c2ccc(C[C@@H](C#N)NC(=O)[C@H]3NC4CCC3CC4)cc2)cc1] | I-2.3.3 | B/FA | 90 |

TABLE 12-continued

| Example | Structure | Educt | Syn./Deprot. Method | Yield [%] |
|---------|-----------|-------|---------------------|-----------|
| 10 | 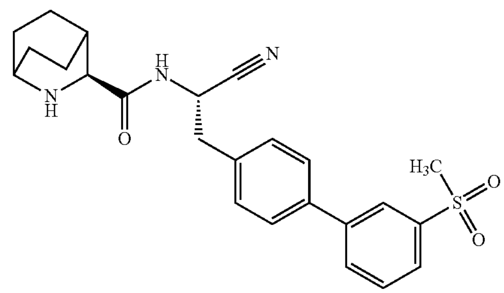 [SMILES: CS(=O)(=O)c1cccc(-c2ccc(C[C@@H](C#N)NC(=O)[C@H]3NC4CCC3CC4)cc2)c1] | I-2.3.4 | B/TSA | 81 |
| 11 | 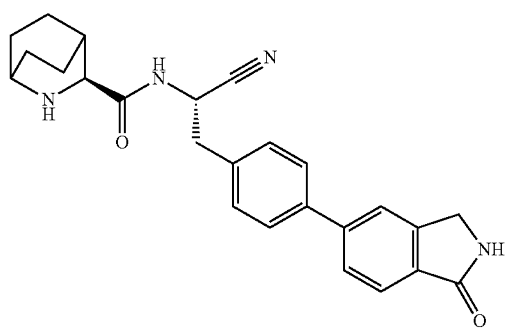 [SMILES: N#C[C@H](Cc1ccc(-c2ccc3c(c2)CNC3=O)cc1)NC(=O)[C@H]1NC2CCC1CC2] | I-2.3.5 | B/TSA | 81 |
| 12 | 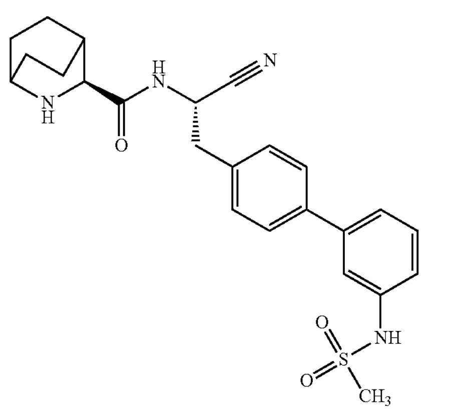 [SMILES: CS(=O)(=O)Nc1cccc(-c2ccc(C[C@@H](C#N)NC(=O)[C@H]3NC4CCC3CC4)cc2)c1] | I-2.3.6 | B/TSA | 85 |
| 13 | 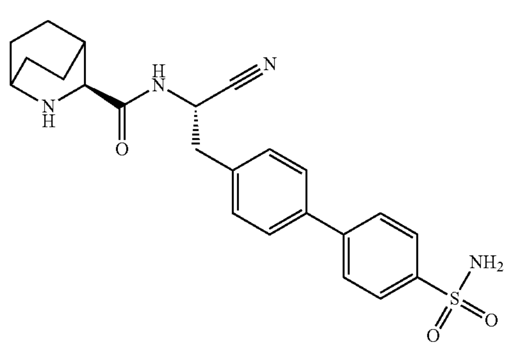 [SMILES: N#C[C@H](Cc1ccc(-c2ccc(S(N)(=O)=O)cc2)cc1)NC(=O)[C@H]1NC2CCC1CC2] | I-2.3.7 | B/FA | 54 |

TABLE 12-continued

| Example | Structure | Educt | Syn./Deprot. Method | Yield [%] |
| --- | --- | --- | --- | --- |
| 14 | 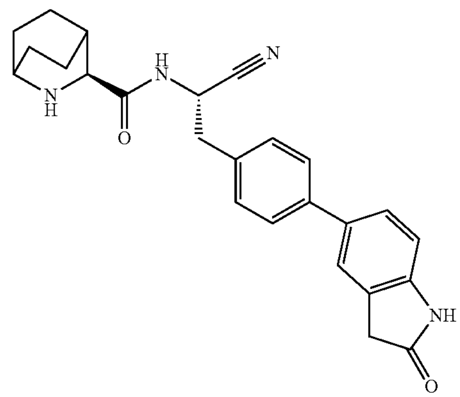 [SMILES: N#C[C@H](Cc1ccc(-c2ccc3c(c2)CC(=O)N3)cc1)NC(=O)[C@H]1NC2CCC1CC2] | I-2.3.8 | B/TSA | 75 |
| 15 | 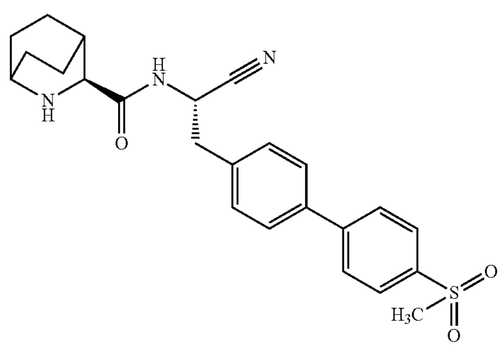 [SMILES: CS(=O)(=O)c1ccc(-c2ccc(C[C@@H](C#N)NC(=O)[C@H]3NC4CCC3CC4)cc2)cc1] | I-2.3.9 | B/FA | 84 |
| 16 | 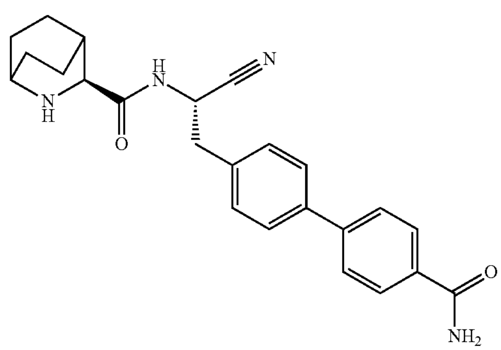 [SMILES: N#C[C@H](Cc1ccc(-c2ccc(C(N)=O)cc2)cc1)NC(=O)[C@H]1NC2CCC1CC2] | I-2.3.10 | B/TSA | 100 |
| 17 | 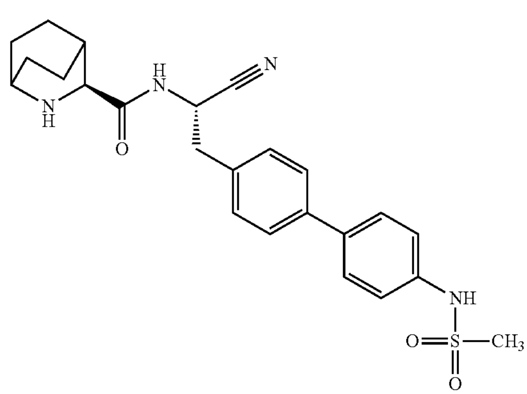 [SMILES: CS(=O)(=O)Nc1ccc(-c2ccc(C[C@@H](C#N)NC(=O)[C@H]3NC4CCC3CC4)cc2)cc1] | I-2.3.11 | B/TSA | 37 |

TABLE 12-continued

| Example | Structure | Educt | Syn./Deprot. Method | Yield [%] |
| --- | --- | --- | --- | --- |
| 18 | 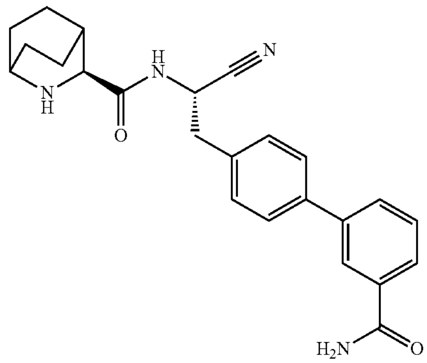 [SMILES: N#C[C@H](Cc1ccc(-c2cccc(C(N)=O)c2)cc1)NC(=O)[C@H]1NC2CCC1CC2] | I-2.3.12 | B/TSA | 66 |
| 19 | 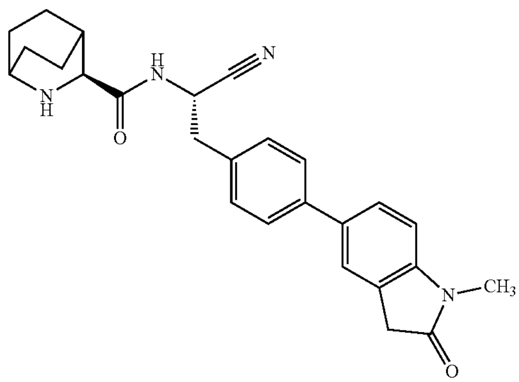 [SMILES: CN1C(=O)Cc2cc(-c3ccc(C[C@@H](C#N)NC(=O)[C@H]4NC5CCC4CC5)cc3)ccc21] | I-2.3.13 | B/TSA | 65 |
| 20 | 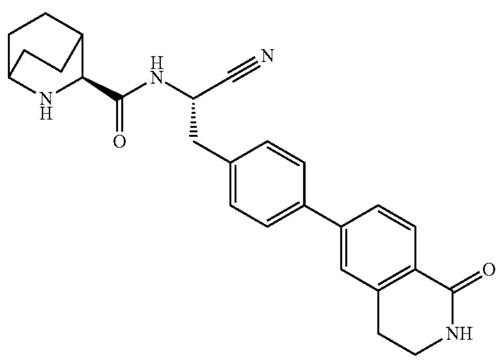 [SMILES: N#C[C@H](Cc1ccc(-c2ccc3c(c2)CCNC3=O)cc1)NC(=O)[C@H]1NC2CCC1CC2] | I-2.3.14 | B/TSA | 69 |
| 21 | 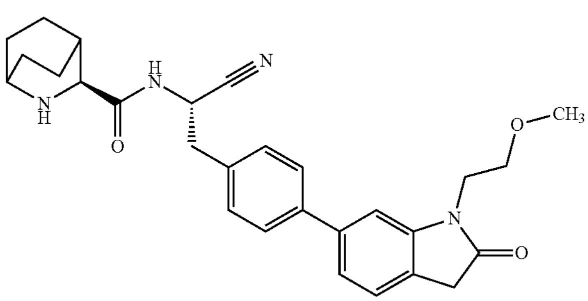 [SMILES: COCCN1C(=O)Cc2ccc(-c3ccc(C[C@@H](C#N)NC(=O)[C@H]4NC5CCC4CC5)cc3)cc21] | I-2.3.15 | B/FA | 88 |

TABLE 12-continued

| Example | Structure | Educt | Syn./Deprot. Method | Yield [%] |
|---|---|---|---|---|
| 22 | 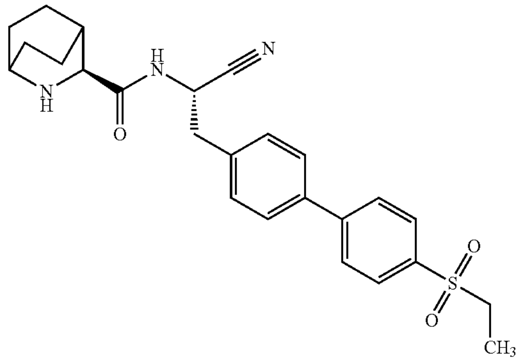 [SMILES: CCS(=O)(=O)c1ccc(-c2ccc(C[C@@H](C#N)NC(=O)[C@H]3NC4CCC3CC4)cc2)cc1] | I-2.3.16 | B/TSA | 58 |
| 23 | 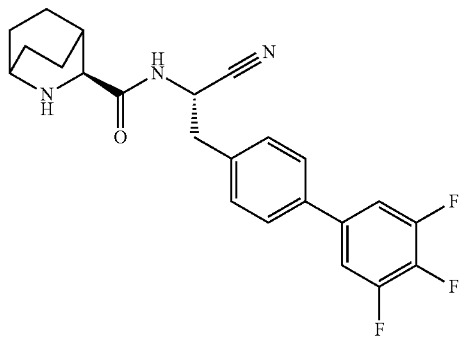 [SMILES: N#C[C@H](Cc1ccc(-c2cc(F)c(F)c(F)c2)cc1)NC(=O)[C@H]1NC2CCC1CC2] | I-2.3.17 | B/TSA | 56 |
| 24 | 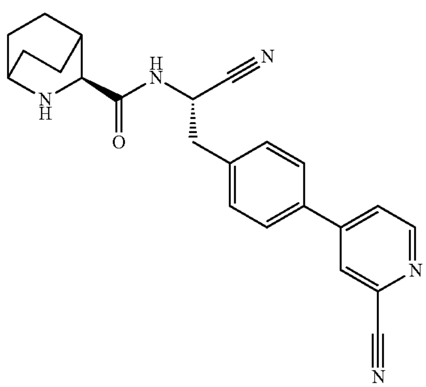 [SMILES: N#Cc1cc(-c2ccc(C[C@@H](C#N)NC(=O)[C@H]3NC4CCC3CC4)cc2)ccn1] | I-2.3.18 | B/TSA | 33 |
| 25 | 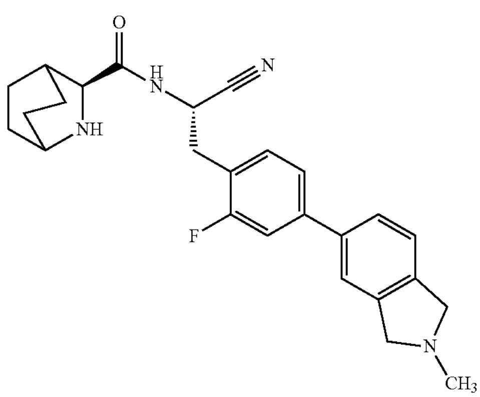 [SMILES: CN1Cc2ccc(-c3ccc(C[C@@H](C#N)NC(=O)[C@H]4NC5CCC4CC5)c(F)c3)cc2C1] | I-1.4.1 | A/TSA | 62 |

TABLE 12-continued

| Example | Structure | Educt | Syn./Deprot. Method | Yield [%] |
|---|---|---|---|---|
| 26 | 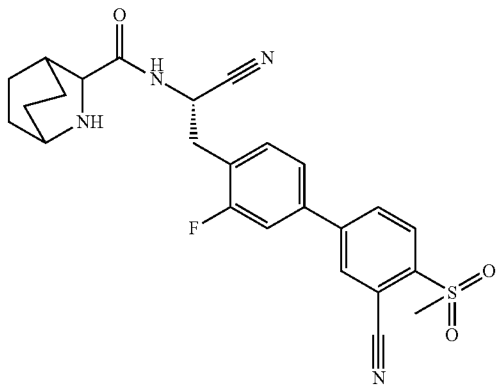 [SMILES: CS(=O)(=O)c1ccc(-c2ccc(C[C@@H](C#N)NC(=O)C3NC4CCC3CC4)c(F)c2)cc1C#N] | I-1.4.3 | A/TSA | 60 |
| 27 | 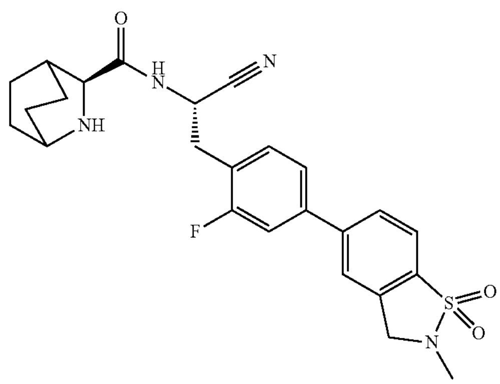 [SMILES: CN1Cc2cc(-c3ccc(C[C@@H](C#N)NC(=O)[C@H]4NC5CCC4CC5)c(F)c3)ccc2S1(=O)=O] | I-1.4.4 | A/TSA | 71 |

Analytical Data of Examples

| Ex. | m/z [M + H]+ | rt [min] | LC-MS-Method |
|---|---|---|---|
| 1 | 481 | 1.08 | V011_S01 |
| 2 | 415 | 0.66 | Z018_S04 |
| 4 | 429 | 1.00 | V002_005 |
| 6 | 429 | 0.57 | Z018_S04 |
| 7 | 403 | 1.15 | V002_005 |
| 8 | 463 | 0.68 | Z018_S04 |
| 9 | 385 | 1.31 | W018_S01 |
| 10 | 438 | 0.67 | Z018_S04 |
| 11 | 415 | 1.31 | Z018_S04 |
| 12 | 453 | 1.13 | W018_S01 |
| 13 | 439 | 1.15 | W018_S01 |
| 14 | 415 | 0.65 | Z018_S04 |
| 15 | 438 | 1.15 | W018_S01 |
| 16 | 403 | 0.62 | Z018_S04 |
| 17 | 453 | 1.08 | W018_S01 |
| 18 | 403 | 1.08 | W018_S01 |
| 19 | 429 | 1.32 | Z018_S04 |
| 20 | 429 | 1.14 | W018_S01 |
| 21 | 473 | 0.61 | Z018_S04 |
| 22 | 452 | 1.27 | W018_S01 |
| 23 | 414 | 1.50 | W018_S01 |
| 24 | 386 | 1.26 | W018_S01 |
| 25 | 433 | 1.21 | V011_S01 |
| 26 | 481 | 0.88 | V018_S01 |
| 27 | 483 | 1.07 | V011_S01 |

Abbreviations

| | |
|---|---|
| ACN | acetonitrile |
| ALOX | aluminium oxide |
| aq. | aqueous |
| BOC | tert. butyloxycyrbonyle-d |
| d | day |
| DCM | dichloromethane |
| DEA | diethylamine |
| DIPEA | n,n-diisopropylethylamine |
| DIPE | diisopropyl ether |
| DMAP | 4-dimethylaminopyridine |
| DMF | n,n-dimethylformamide |
| DMSO | dimethyl sulfoxide |
| EA | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| MSA | methanesulfonic acid |
| MeTHF | methyl tetrahydrofuran |
| RT, r.t. | room temperature |
| rt | retention time |
| sat. | saturated |
| SI | trimethylsilyl iodide |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

PHARMACOLOGICAL DATA

Other features and advantages of the present invention will become apparent from the following more detailed examples which illustrate, by way of example, the principles of the invention.

Inhibition of Human DPPI (Cathepsin C)

Materials: Microtiterplates (Optiplate-384 F) were purchased from PerkinElmer (Prod. No. 6007270). The substrate Gly-Arg-AMC was from Biotrend (Prod.-No. 808756 Custom peptide). Bovine serum albumin (BSA; Prod. No. A3059) and Dithiothreitol (DTT; Prod. No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPP1 inhibitor Gly-Phe-DMK was purchased from MP Biomedicals (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM $NaH_2PO_4$, 150 mM NaCl adjusted to pH 6.0 with HCl Assay Conditions:

The recombinant human DPPI was diluted in TAGZyme buffer to 1 U/ml (38.1 µg/ml, respectively), and then activated by mixing in a 1:2 ratio with a Cysteamine aqueous solution (2 mM) and incubating for 5 min at room temperature.

Five uL test compound (final concentration 0.1 nM to 100 µM) in aqua bidest (containing 4% DMSO, final DMSO concentration 1%) were mixed with 10 µL of DPPI in MES buffer (final concentration 0.0125 ng/µL) and incubated for 10 min. Then, 5 µL of substrate in MES buffer (final concentration 50 µM) were added. The microtiter plates were then incubated at room temperature for 30 min. Then, the reaction was stopped by adding 10 µL of Gly-Phe-DMK in MES-buffer (final concentration 1 µM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% BSA) as reference for non-inhibited enzyme activity (100% Ctl; high values) and wells with inhibitor (Gly-Phe-DMK, in bidest+1% DMSO+ 0.075% BSA, final concentration 1 µM) as controls for background fluorescence (0% Ctl; low values).

The analysis of the data was performed by calculating the percentage of fluorescence in the presence of test compound in comparison to the fluorescence of the vehicle control after subtracting the background fluorescence using the following formula:

(RFU(sample)−RFU(background))*100/(RFU(control)−RFU(background))

Data from these calculations were used to generate $IC_{50}$ values for inhibition of DPPI, respectively.

| Ex. | Inhibition of DPPI IC50 [µM] |
|---|---|
| 1 | 0.0301 |
| 2 | 0.0501 |
| 4 | 0.0322 |
| 6 | 0.0522 |
| 7 | 0.0664 |
| 8 | 0.0702 |
| 9 | 0.0730 |
| 10 | 0.0735 |
| 11 | 0.0867 |
| 12 | 0.0974 |
| 13 | 0.1023 |
| 14 | 0.1028 |
| 15 | 0.1105 |
| 16 | 0.1180 |
| 17 | 0.1237 |
| 18 | 0.1307 |
| 19 | 0.1337 |
| 20 | 0.1367 |
| 21 | 0.1598 |
| 22 | 0.1644 |
| 23 | 0.2437 |
| 24 | 0.2485 |
| 25 | 0.0980 |
| 26 | 0.0278 |
| 27 | 0.0733 |

Inhibition of Human Cathepsin K

Materials: Microtiterplates (Optiplate-384 F were purchased from PerkinElmer (Prod. No. 6007270). The substrate Z-Gly-Pro-Arg-AMC was from Biomol (Prod.-No. P-142). L-Cysteine (Prod. No. 168149) was from Sigma. Sodium acetate was from Merck (Prod.-No. 6268.0250), EDTA was from Fluka (Prod.-No. 03680). The inhibitor E-64 was purchased from Sigma (Prod.-No. E3132). The recombinant human Cathepsin K proenzyme was purchased from Biomol (Prod. No. SE-367). All other materials were of highest grade commercially available.

The following buffers were used: Activation buffer: 32.5 mM sodium acetate, adjusted to pH 3.5 with HCl; Assay buffer: 150 mM sodium acetate, 4 mM EDTA, 20 mM L-Cysteine, adjusted to pH 5.5 with HCl, Assay Conditions:

To activate the proenzyme, 5 µl procathepsin K were mixed with 1 ul activation buffer, and incubated at room temperature for 30 min.

5 µL test compound (final concentration 0.1 nM to 100 µM) in aqua bidest (containing 4% DMSO, final DMSO concentration 1%) were mixed with 10 uL of Cathepsin K in assay buffer (final concentration 2 ng/µL) and incubated for 10 min. Then 5 µL of substrate in assay buffer (final concentration 12.5 µM) were added. The plates were then incubated at room temperature for 60 min. Then, the reaction was stopped by adding 10 µL of E64 in assay buffer (final concentration 1 µM). The fluorescence in the wells was determined using a Molecular Devices SpectraMax M5 Fluorescence Reader (Ex 360 nm, Em 460 nm).

Each assay microtiter plate contains wells with vehicle controls (1% DMSO in bidest) as reference for non-inhibited enzyme activity (100% Ctl; high values) and wells with inhibitor (E64 in bidest+1% DMSO, final concentration 1 µM) as controls for background fluorescence (0% Ctl; low values). The analysis of the data was performed by calculating the percentage of fluorescence in the presence of test compound in comparison to the fluorescence of the vehicle control after subtracting the background fluorescence:

(RFU(sample)−RFU(background))*100/(RFU(control)−RFU(background))

Data from these calculations were used to generate $IC_{50}$ values for inhibition of Cathepsin K, respectively.

| Ex. | Inhibition of Cathepsin K IC50 [μM] |
| --- | --- |
| 1 | 2.7 |
| 2 | 4.2 |
| 4 | 6.3 |
| 7 | 5.7 |
| 8 | 5.3 |
| 9 | 14.8 |
| 10 | 5.3 |
| 11 | 11.0 |
| 12 | 9.9 |
| 13 | 10.8 |
| 17 | 6.7 |
| 18 | 9.7 |

Determination of Neutrophil Elastase Activity in U937 Cytosolic Lysate Preparation after Incubation with Test Compound Materials:

Optiplate 384F were purchased from PerkinElmer (Prod. No. #6007270). 24 well Nunclon cell culture plates (No. 142475) and 96 well plates (No. 267245) were from Nunc. Dimethylsulfoxid (DMSO) was from Sigma (Prod. No. D8418). Nonidet-P40 (NP40) was from USBiological (Prod. No. N3500)

Substrate, specific for Neutrophil elastase, was from Bachem (MeOSuc-Ala-Ala-Pro-Val-AMC; Prod. No. I-1270).

Human neutrophil elastase was from Calbiochem (Prod. No. 324681)

Buffers:
Tris-buffer (100 mM Tris; 1M NaCL; pH 7.5)
Tris-buffer+ HSA 0.1%; Human Serum Albumin from Calbiochem (Cat#. 126658)
Serine-protease buffer (20 mM Tris; 100 mM NaCL; pH 7.5)+0.1% HSA
Serine protease lysis buffer: 20 mM Tris-HCL; 100 mM NaCl pH 7.5; +0.2% Nonidet-P40;
PBS: phosphate buffered saline, without Ca and Mg, from Gibco Cell Culture:
U937 from ECACC (Cat. No. 85011440) cultured in suspension at 37° C. and 5% CO2.
Cell density: 0.2-1 Mio. Cells/ml.
Medium: RPMI1640 GlutaMAX (No. 61870) with 10% FCS from Gibco Cell Seeding and Treatment:
Compounds in 100% DMSO were diluted in Medium (—FCS) with 10% DMSO and further diluted according to the experiment planned.

20 μl of the compound solution was transferred in the respective wells of the 24 well plate and diluted with 2 ml cell suspension/well containing 1,105 cells/ml (final concentration of DMSO=0.1%). Compound dilution factor=100

Compounds (up to 7 concentrations) were tested in triplicates with 3 wells for the DMSO 0.1% control, incubatet for 48 hours without medium change at 37° C., 5% CO2 and 95% relative humidity.

Cell Harvesting and Cell Lysate:
Transfer the cell suspension in 2.2 ml Eppendorf cups. Separate cells from medium by centrifugation (400×g; 5 min; RT); discard the supernatant. Resuspend in 1 ml PBS; centrifugation (400×g; 5 min; RT); wash cells twice with PBS. Add 100 μl Serin lysis buffer (ice cold) to the cell pellet; resuspend the pellet and store on ice for 15 minutes. Remove debris by centrifugation at 15000×g for 10 min at 4° C. Transfer 80-100 μl lysate supernatant in 96 well plate and store immediately at −80° C.

Neutrophil Elastase Activity Assay:
Frozen lysates were thawn at 37° C. for 10 minutes and stored on ice. Protein content was determined with Bradford protein assay. Lysates were diluted to 0.2-0.5 mg/ml protein in serine protease buffer+ HSA.

Standard: NE (100 μg/ml stocksolution in Tris-buffer; stored at −80° C.) was diluted in Tris-buffer+HSA to 750 ng/ml, and further serially diluted 1:2 for the standard curve.

Buffer, blank, standard and lysate samples were transferred into 384 well plate

Pipetting Plan
Blank: 5 μl Tris-buffer+10 μl Tris-buffer+ HSA+5 μl Substrate
Standard: 5 μl Tris-buffer+10 μl NE (diff.conc.)+5 μl Substrate
Lysate: 5 μl Tris-buffer+10 μl Lysat+5 μl Substrate The increase in fluorescence (Ex360 nm/Em 460 nm) is determined over 30 minutes with a Molecular Device Spectramax M5 Fluorescence Reader. Kinetic Reduction (Vmax units/sec); 4 vmax points. The amount of neutrophil elastase (ng/ml) is calculated using the standard curve and the Spectramax software. The result is interpolated to ng/mg lysate protein using excel formula functions. Percent inhibition in the compound-treated lysate samples is calculated relative to the DMSO-treated control-sample (100-(compound-sample*100)/control-sample)

A test compound will give values between 0% and 100% inhibition of neutrophil elastase. IC50 is calculated using Graphpad Prism; nonlinear fitting (log(inhibitor) vs. response—Variable slope).

The IC50 value is interpolated as the concentration of test compound which leads to a neutrophil elastase activity reduction of 50% (relative to the DMSO-treated control).

| Example | Reduction of NE-activity in U937 cells IC50 [μM] |
| --- | --- |
| 1 | 0.134 |
| 2 | 0.281 |
| 4 | 0.050 |
| 7 | 0.561 |
| 8 | 0.469 |
| 10 | 0.426 |
| 11 | 0.328 |
| 12 | 0.450 |

Determination of Metabolic Stability with Human Liver Microsomes

The metabolic degradation of the test compound is assayed at 37° C. with pooled human liver microsomes. The final incubation volume of 100 μl per time point contains TRIS buffer pH 7.6 (0.1 M), magnesium chloride (5 mM), microsomal protein (1 mg/ml) and the test compound at a final concentration of 1 μM. Following a short preincubation period at 37° C., the reactions are initiated by addition of beta-nicotinamide adenine dinucleotide phosphate, reduced form (NADPH, 1 mM) and terminated by transfering an aliquot into acetonitrile after different time points. Additionally, the NADPH-independent degradation is monitored in incubations without NADPH, terminated at the last time point. The [%] remaining test compound after NADPH independent incubation is reflected by the parameter c(control) (metabolic stability). The quenched incubations are pelleted by centrifugation (10,000 g, 5 min). An aliquot of the supernatant is assayed by LC-MS/MS for the amount of parent compound.

The half-life (t½ INVITRO) is determined by the slope of the semilogarithmic plot of the concentration-time profile. The intrinsic clearance (CL_INTRINSIC) is calculated by considering the amount of protein in the incubation:

CL_INTRINSIC[µl/min/mg protein]=(ln 2/(half-life [min]*protein content[mg/ml]))*1,000.

The half-life (t½ INVITRO) values of selected compounds in the metabolic stability assay described above are listed in the following table

| Ex. | In vitro stability in human liver microsome incubations t½ [min] |
|---|---|
| 1 | 120 |
| 2 | 120 |
| 4 | 88 |
| 7 | >130 |
| 8 | >130 |
| 9 | >130 |
| 10 | >130 |
| 11 | >130 |
| 12 | 64 |

COMBINATIONS

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DP1-receptor modulators, Thromboxane receptor antagonists, CCR3 antagonists, CCR$^4$ antagonists, CCR1 antagonists, CCR5 antagonists, CCR6 antagonists, CCR7 antagonists, CCR8 antagonists, CCR9 antagonists, CCR30 antagonists, CXCR$^3$ antagonists, CXCR$^4$ antagonists, CXCR$^2$ antagonists, CXCR$^1$ antagonists, CXCR5 antagonists, CXCR6 antagonists, CX3CR$^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Matriptase-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

INDICATIONS

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency, bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, polyangiitis (Wegener Granulomatosis) and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

1. A method of treating asthma and allergic diseases, gastrointestinal inflammatory diseases, eosinophilic diseases, chronic obstructive pulmonary disease, infection by pathogenic microbes, rheumatoid arthritis or atherosclerosis comprising administering to a patient a therapeutically effective amount of a compound of formula 1

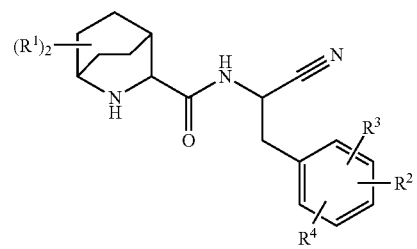

wherein $R^1$ is independently selected from among H, $C_{1-6}$-alkyl-, halogen, HO—, $C_{1-6}$-alkyl-O—, $H_2N$—, $C_{1-6}$-alkyl-HN—, $(C_{1-6}$-alkyl$)_2N$— and $C_{1-6}$-alkyl-C(O)HN—;

or two $R^1$ are together $C_{1-4}$-alkylene;

$R^2$ is selected from among $R^{2.1}$;

aryl-; optionally substituted with one, two or three residues independently selected from $R^{2.1}$; optionally substituted with one $R^{2.3}$;

$C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$; — and $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$ or $R^2$ and $R^4$ are together with two adjacent carbon atoms of the phenyl ring a 5- or 6-membered aryl or heteroaryl, containing one, two or three heteroatoms independently selected from among S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$;

$R^{2.1}$ is independently selected from among H, halogen, NC—, O=, HO—, H-A-, H-A-$C_{1-6}$-alkylene-, $R^{2.1.1}$-A-, $C_{1-6}$-alkyl-A-, $C_{3-8}$-cycloalkyl-A-, $C_{1-6}$-haloalkyl-A-, $R^{2.1.1}$—$C_{1-6}$-alkylene-A-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$—$C_{1-6}$-alkylene-A-$C_{1-6}$-alkylene-, $R^{2.1.1}$-A-$C_{1-6}$-alkylene-, HO—$C_{1-6}$-alkylene-A-, HO—$C_{1-6}$-alkylene-A-$C_{1-6}$-alkylene-, $C_{1-6}$-alkyl-O—$C_{1-6}$-alkylene-A- and $C_{1-6}$-alkyl-O—$C_{1-6}$-alkylene-A-$C_{1-6}$-alkylene- $R^{2.1.1}$ is independently selected from among
- aryl-; optionally substituted independently from each other with one, two or three $R^{2.1.1.1}$;
  - $C_{5-10}$-heteroaryl-; containing one, two, three or four heteroatoms independently selected from among S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; — and
  - $C_{5-10}$-heterocyclyl-; containing one, two, three or four heteroatoms independently selected from among S, S(O), S(O)$_2$, O and N, wherein the ring is fully or partially saturated, wherein carbon atoms of the ring are optionally and independently from each other substituted with one, two or three or four $R^{2.1.1.1}$; wherein nitrogen atoms of the ring are optionally and independently from each other substituted with one, two or three $R^{2.1.1.2}$;

$R^{2.1.1.1}$ is independently selected from among halogen, HO—, O=, $C_{1-6}$-alkyl-, $C_{1-6}$-alkyl-O—, $C_{1-6}$-haloalkyl-, $C_{1-6}$-haloalkyl-O— and $C_{3-8}$-cycloalkyl-;

$R^{2.1.1.2}$ is independently selected from among O=, $C_{1-6}$-alkyl-, $C_{1-6}$-haloalkyl-; $C_{3-8}$-cycloalkyl-, $C_{1-6}$-alkyl-O—$C_{1-6}$-alkyl-, H(O)C—, $C_{1-6}$-alkyl-(O)C—, tetrahydrofuranylmethyl- and tetrahydropyranylmethyl-;

$R^{2.2}$ is independently selected from among H-A-$C_{1-6}$-alkylene-, $C_{3-8}$-cycloalkyl-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$-A-$C_{1-6}$-alkylene-, $C_{1-6}$-alkyl-S(O)$_2$—, $C_{1-6}$-alkyl-C(O)— and $R^{2.1.1}$-A-;

$R^{2.3}$ and $R^4$ are together selected from
among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, $R^{2.3}$, $R^{2.3}$, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-;

$R^{2.3.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4}$ and $R^4$ are together selected from
among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)— and —N($R^{2.4.1}$)C($R^{2.4.2}$)$_2$—, —$C_{1-4}$-alkylene-; and $R^{2.4.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.5}$ and $R^4$ are together selected from among —C($R^{2.5.1}$)=, =C($R^{2.5.1}$)— and —N=; and $R^{2.5.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^3$ is H or F;

$R^4$ is independently selected from among H, F, Cl, phenyl-H$_2$C—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from
among —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=)S(O)—, —S(=N$R^5$)$_2$—N($R^5$)—, —N($R^5$)(N$R^5$=)$_2$S—, —C($R^5$)=C($R^5$)—, —C=C—, —C(O)O—, —OC(O)—, —C(O)—, —S(O)—, —S(O)$_2$—, —S(=N$R^5$)—, —S(O)(=N$R^5$)—, —S(=N$R^5$)$_2$—, —($R^5$)(O)S =N—, —($R^5$N=)(O)S— and —N=(O)($R^5$)S—;

$R^5$ is independently selected from among H, $C_{1-6}$-alkyl- and NC—;

or a pharmaceutically acceptable salt thereof.

2. The method according to claim 1, wherein $R^1$ is $R^{1.a}$ and $R^{1.a}$ is independently selected from among H, $C_{1-4}$-alkyl-, F— and HO—.

3. The method according to claim 1, wherein $R^4$ is $R^{4.a}$ and $R^{4.a}$ is H, F, Cl, phenyl-H$_2$C—O—, HO—, $C_{1-4}$-alkyl-, $C_{3-6}$-cycloalkyl-, $C_{1-4}$-alkyl-O— and $C_{1-4}$-haloalkyl-O—.

4. The method according to claim 1, wherein $R^4$ is $R^{4.b}$ and $R^{4.b}$ is H or F.

5. The method according to claim 1, wherein A is A$^a$ and A$^a$ is a bond or independently selected from
among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$—, —($R^5$)(O)S=N—, —($R^5$N=)(O)S— and —N=(O)($R^5$)S—, and $R^5$ is $R^{5.a}$ and $R^{5.a}$ is independently selected from among H, $C_{1-4}$-alkyl- and NC—.

6. The method according to claim 1, wherein $R^2$ is $R^{2.1}$ and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$- alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and R$^{2.1.1}$ is R$^{2.1.1.a}$ and R$^{2.1.1.a}$ selected from among aryl-, optionally substituted independently from each other with one, two or three residues independently selected from R$^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; — and C$_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; and R$^{2.1.1.1}$ is independently selected from among halogen, HO—, O=, C$_{1-4}$-alkyl-, C$_{1-4}$-alkyl-O—, C$_{1-4}$-haloalkyl-, C$_{1-4}$-haloalkyl-O— and C$_{3-6}$-cycloalkyl-; and R$^{2.1.1.2}$ is independently selected from among O=, C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl.

7. The method according to claim 1, wherein R$^2$ is R$^{2.d}$ and R$^{2.d}$ is phenyl; optionally substituted with one, two or three residues independently selected from R$^{2.1}$ and R$^{2.1}$ is R$^{2.1.a}$ and R$^{2.1.a}$ is selected from among H, halogen, NC—, O=, HO—, H-A-, H-A-C$_{1-4}$-alkylene-, R$^{2.1.1}$-A-, C$_{1-4}$-alkyl-A-, C$_{3-6}$-cycloalkyl-A-, C$_{1-4}$-haloalkyl-A-, R$^{2.1.1}$—C$_{1-4}$-alkylene-A-, C$_{1-4}$-alkyl-A-C$_{1-4}$alkylene-, C$_{3-6}$-cycloalkyl-A-C$_{1-4}$-alkylene-, C$_{1-4}$-haloalkyl-A-C$_{1-4}$-alkylene-, R$^{2.1.1}$—C$_{1-4}$-alkylene-A-C$_{1-4}$-alkylene-, R$^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and R$^{2.1.1}$ is R$^{2.1.1.a}$ and R$^{2.1.1.a}$ is selected from among aryl-, optionally substituted independently from each other with one, two or three residues independently selected from R$^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; — and C$_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; and R$^{2.1.1.1}$ is independently selected from among halogen, HO—, O=, C$_{1-4}$-alkyl-, C$_{1-4}$-alkyl-O—, C$_{1-4}$-haloalkyl- and C$_{1-4}$-haloalkyl-O—, C$_{3-6}$-cycloalkyl-; and R$^{2.1.1.2}$ is independently selected from among O=, C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl.

8. The method according to claim 1, wherein R$^2$ is R$^{2.g}$ and R$^{2.g}$ is selected from among

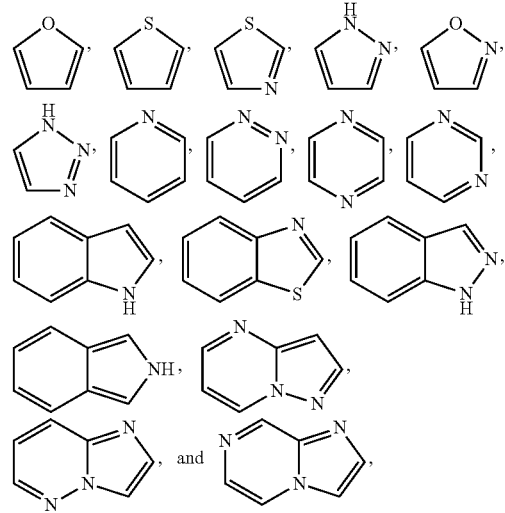

wherein carbon atoms of the ring are optionally and independently from each other substituted with one, two or three R$^{2.1}$; wherein possibly available nitrogen atoms of the ring are optionally and independently from each other substituted with R$^{2.2}$; and R$^{2.1}$ is R$^{2.1.a}$ and R$^{2.1.a}$ is selected from among H, halogen, NC—, O=, HO—, H-A-, H-A-C$_{1-4}$-alkylene-, R$^{2.1.1}$-A-, C$_{1-4}$-alkyl-A-, C$_{3-6}$-cycloalkyl-A-, C$_{1-4}$-haloalkyl-A-, R$^{2.1.1}$—C$_{1-4}$-alkylene-A-, C$_{1-4}$-alkyl-A-C$_{1-4}$-alkylene, C$_{3-6}$-cycloalkyl-A-C$_{1-4}$-alkylene-, C$_{1-4}$-haloalkyl-A-C$_{1-4}$-alkylene-, R$^{2.1.1}$—C$_{1-4}$-alkylene-A-C$_{1-4}$-alkylene-, R$^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and R$^{2.1.1}$ is R$^{2.1.1.a}$ and R$^{2.1.1.a}$ is selected from among aryl-, optionally substituted independently from each other with one, two or three residues independently selected from R$^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; — and C$_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three R$^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl-; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

9. The method according to claim 1, wherein $R^2$ is $R^{2.j}$ and $R^{2.j}$ is selected from among

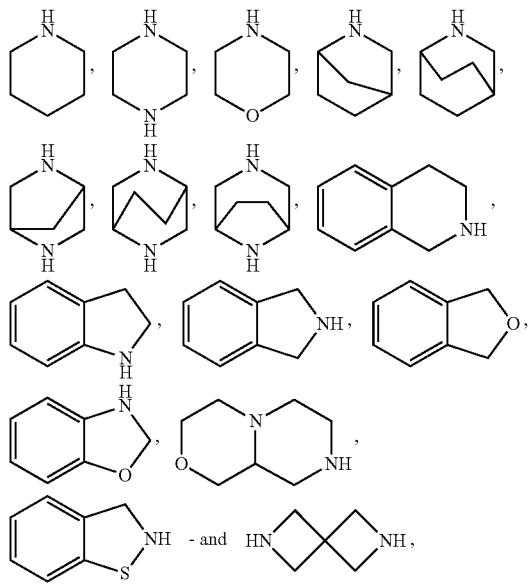

wherein carbon atoms of the ring are optionally and independently from each other substituted with one, two or three $R^{2.1}$; wherein possibly available nitrogen atoms of the ring are optionally and independently from each other substituted with $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; — and
  $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl-; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— — and $R^{2.1.1}$-A-.

10. The method according to claim 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from among S, S(O), S(O)$_2$, O and N, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$; and $R^{2.1}$ is $R^{2.1.a}$ and $R^{2.1.a}$ is selected from among H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$alkylene-, $C_{3-6}$-cycloalkyl-A-$C_{1-4}$-alkylene-, $C_{1-4}$-haloalkyl-A-$C_{1-4}$-alkylene, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from among
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from among halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from among O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from among H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— — and $R^{2.1.1}$-A-.

11. The method according to claim 1, wherein $R^2$ is $R^{2.t}$ and $R^{2.t}$ is selected from among the substituents (a2) to (g2)

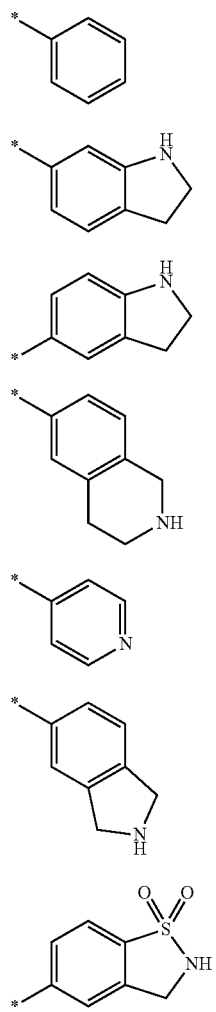

wherein carbon atoms of the rings are optionally and independently from each other substituted with one, two or three $R^{2.1}$; wherein a nitrogen atom of the ring is optionally substituted with $R^{2.2}$, or a salt thereof.

12. The method according to claim 1, wherein $R^1$ is $R^{1.b}$ and $R^{1.b}$ is H;

$R^2$ is selected from among phenyl-; optionally substituted with one or two residues independently selected from $R^{2.1}$; optionally substituted with one $R^{2.3}$;

$C_5$-heteroaryl-; containing two or three independently selected from among S, O and N, wherein carbon atoms of the ring are optionally and independently from each other substituted with one $R^{2.1}$; wherein nitrogen atoms of the ring are optionally and independently from each other substituted with one $R^{2.2}$;

monocyclic $C_6$-heterocyclyl containing one or two nitrogen atoms, wherein the ring is fully or partially saturated, wherein carbon atoms of the ring are optionally and independently from each other substituted with one $R^{2.1}$; wherein nitrogen atoms of the ring are optionally and independently from each other substituted with one $R^{2.2}$;

bicyclic $C_{9\ or\ 10}$-heterocyclyl-; containing one, two, three or four heteroatoms independently selected from among S(O)$_2$, O and N, wherein the ring is fully or partially saturated, wherein carbon atoms of the ring are optionally and independently from each other substituted with one, two or three $R^{2.1}$; wherein nitrogen atoms of the ring are optionally and independently from each other substituted with one $R^{2.2}$;

$R^{2.1}$ is independently selected from among halogen, NC—, O=, H-A-, H-A-$C_{1-4}$-alkylene-, $R^{2.1.1}$-A-, A-, $C_{1-4}$-alkyl-A-, $C_{3-6}$-cycloalkyl-A-, $R^{2.1.1}$—$C_{1-4}$-alkylene-A-, $C_{1-4}$-alkyl-A-$C_{1-4}$-alkylene- and HO—$C_{1-4}$-alkylene-A-$C_{1-4}$-alkylene-;

$R^{2.1.1}$ is independently selected from among phenyl-;- and $C_{5\ or\ 6}$-heterocyclyl-; containing one or two heteroatoms independently selected from among 0 and N, wherein the ring is fully or partially saturated, wherein nitrogen atoms of the ring are optionally and independently from each other substituted with one $C_{1-4}$-alkyl-;

$R^{2.2}$ is independently selected from among H-A-$C_{1-4}$-alkylene-, $C_{3-6}$-cycloalkyl-, $C_{1-4}$-alkyl-A-$C_{1-4}$-alkylene-, $R^{2.1.1}$-A-$C_{1-4}$-alkylene- and $C_{1-4}$-alkyl-C(O)—;

$R^{2.3}$ and $R^4$ are together a group selected from among —N($R^{2.3.1}$)—, —C(O)N($R^{2.3.2}$)— — and —N($R^{2.3.1}$)C(O)—;

$R^{2.3.1}$ is independently selected from among H— and H$_3$C—;

$R^3$ is H, F;

$R^4$ is $R^{4.b}$ and $R^{4.b}$ and is H or F;

A is a bond or independently selected from among —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$— and —N=(O)($R^5$)S—;

$R^5$ is independently selected from among H— and $C_{1-4}$-alkyl-;

or a salt thereof.

13. The method according to claim 1 wherein the compound is a compound of formula 1'

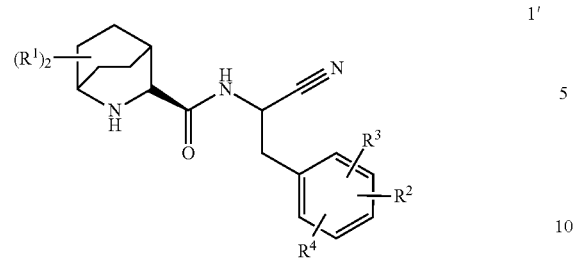
wherein R¹, R², R³ and R⁴ have the meaning of claim 1.
* * * * *